US008906032B2

(12) United States Patent
Hanson et al.

(10) Patent No.: US 8,906,032 B2
(45) Date of Patent: Dec. 9, 2014

(54) INSTRUMENTS FOR A VARIABLE ANGLE APPROACH TO A JOINT

(75) Inventors: Shaun B. Hanson, West Chester, PA (US); Charanpreet S. Bagga, Basking Ridge, NJ (US); Christopher D. Mandeen, Bethlehem, PA (US); Bradford S. Tucker, Ocean City, NJ (US)

(73) Assignee: Zimmer Knee Creations, Inc., Exton, PA (US)

( * ) Notice: Subject to any disclaimer, the term of this patent is extended or adjusted under 35 U.S.C. 154(b) by 365 days.

(21) Appl. No.: 12/950,154

(22) Filed: Nov. 19, 2010

(65) Prior Publication Data
US 2011/0125159 A1   May 26, 2011

Related U.S. Application Data

(60) Provisional application No. 61/263,170, filed on Nov. 20, 2009, provisional application No. 61/310,897, filed on Mar. 5, 2010, provisional application No. 61/311,152, filed on Mar. 5, 2010.

(51) Int. Cl.
| A61B 17/58 | (2006.01) |
| A61B 17/60 | (2006.01) |
| A61F 2/00 | (2006.01) |
| A61B 17/17 | (2006.01) |
| A61B 17/88 | (2006.01) |

(52) U.S. Cl.
CPC ......... *A61B 17/1764* (2013.01); *A61B 17/1742* (2013.01); *A61B 17/8805* (2013.01); *A61B 2017/1775* (2013.01); *A61B 2017/1778* (2013.01)
USPC .......................................................... 606/96

(58) Field of Classification Search
USPC .................................. 606/96–99, 104, 87, 64
See application file for complete search history.

(56) References Cited

U.S. PATENT DOCUMENTS

| 2,697,433 A | 12/1954 | Zehnder |
| 3,913,187 A | 10/1975 | Okuda |

(Continued)

FOREIGN PATENT DOCUMENTS

| CN | 101048111 A | 10/2007 |
| CN | 101102724 A | 1/2008 |

(Continued)

OTHER PUBLICATIONS

May 12, 2008 Riddle Memorial Hospital, Medial, PA 19063 Operative Report. Surgeon: Peter F Sharkey, M.D.; Right knee, medial tibial plateau; a cannulated bone biopsy needle was placed into the bone under fluoroscopic guidance; Implant used: Stryker Orthopedics Hydroset (Bone Substitute Material); Surgeon also expressed difficulty in injecting the bone substitute.

(Continued)

*Primary Examiner* — Andrew Yang
(74) *Attorney, Agent, or Firm* — Schwegman Lundberg & Woessner, P.A.

(57) ABSTRACT

Instruments and associated methods are disclosed for treating joints, and particularly bone tissue. One of these instruments may be a positioning instrument for controlled delivery of a device to a target site of the bone tissue being treated. The positioning instrument may comprise a main body extending at one end into an indicator probe for visual determination of a target site of a bone to be treated, and at an opposite end into a handle. A rail extends from the main body. The instrument also includes an alignment guide having a device portal for insertion of a device therethrough, the alignment guide being detachable and movable along a length of the rail. The device may comprise an implant insertion tool, an injection catheter, a cavity creation tool such as a bone drill, for example, or the device may be an implantable device.

42 Claims, 13 Drawing Sheets

(56) References Cited

U.S. PATENT DOCUMENTS

| | | |
|---|---|---|
| 3,988,783 A | 11/1976 | Treace |
| 4,037,592 A * | 7/1977 | Kronner .................... 606/97 |
| 4,108,165 A | 8/1978 | Kopp et al. |
| 4,360,012 A | 11/1982 | Mcharrie et al. |
| 4,653,487 A | 3/1987 | Maale |
| 4,815,454 A | 3/1989 | Dozier, Jr. |
| 4,883,048 A | 11/1989 | Purnell et al. |
| 4,911,153 A | 3/1990 | Border |
| 4,920,958 A | 5/1990 | Walt et al. |
| 4,964,861 A | 10/1990 | Agee et al. |
| 5,098,383 A | 3/1992 | Hemmy et al. |
| 5,163,940 A | 11/1992 | Bourque |
| 5,178,164 A | 1/1993 | Allen |
| 5,247,934 A | 9/1993 | Wehrli et al. |
| 5,298,254 A | 3/1994 | Prewett et al. |
| 5,324,295 A | 6/1994 | Shapiro |
| 5,342,363 A | 8/1994 | Richelsoph |
| 5,370,646 A | 12/1994 | Reese et al. |
| 5,439,684 A | 8/1995 | Prewett et al. |
| 5,514,137 A | 5/1996 | Coutts |
| 5,556,429 A | 9/1996 | Felt |
| 5,595,193 A | 1/1997 | Walus et al. |
| 5,609,636 A | 3/1997 | Kohrs et al. |
| 5,618,549 A | 4/1997 | Patat et al. |
| 5,681,320 A | 10/1997 | McGuire |
| 5,741,266 A | 4/1998 | Moran et al. |
| 5,743,916 A | 4/1998 | Greenberg et al. |
| 5,755,809 A | 5/1998 | Cohen |
| 5,766,221 A | 6/1998 | Benderev et al. |
| 5,827,289 A | 10/1998 | Reiley et al. |
| 5,868,749 A | 2/1999 | Reed |
| 5,888,220 A | 3/1999 | Felt et al. |
| 5,891,150 A | 4/1999 | Chan |
| 5,928,239 A | 7/1999 | Mirza |
| 5,968,047 A | 10/1999 | Reed |
| 5,972,015 A | 10/1999 | Scribner et al. |
| 6,010,502 A | 1/2000 | Bagby |
| 6,036,696 A | 3/2000 | Lambrecht et al. |
| 6,039,742 A | 3/2000 | Krettek et al. |
| 6,048,346 A | 4/2000 | Reiley et al. |
| 6,066,154 A | 5/2000 | Reiley et al. |
| 6,110,211 A | 8/2000 | Weiss |
| 6,111,164 A | 8/2000 | Rainey et al. |
| 6,120,511 A | 9/2000 | Chan |
| 6,140,452 A | 10/2000 | Felt |
| 6,143,030 A | 11/2000 | Schroder |
| 6,162,225 A | 12/2000 | Gertzman et al. |
| 6,214,013 B1 | 4/2001 | Lambrecht et al. |
| 6,235,043 B1 | 5/2001 | Reiley |
| 6,241,734 B1 | 6/2001 | Scribner |
| 6,248,110 B1 | 6/2001 | Reiley |
| 6,248,131 B1 | 6/2001 | Felt et al. |
| 6,254,605 B1 | 7/2001 | Howell |
| 6,267,770 B1 | 7/2001 | Truwit |
| 6,270,528 B1 | 8/2001 | Mckay |
| 6,285,901 B1 | 9/2001 | Taicher et al. |
| 6,287,313 B1 | 9/2001 | Sasso |
| 6,294,187 B1 | 9/2001 | Boyce et al. |
| 6,306,177 B1 | 10/2001 | Felt |
| 6,342,056 B1 | 1/2002 | Mac-Thiong et al. |
| 6,358,251 B1 | 3/2002 | Mirza |
| 6,368,322 B1 | 4/2002 | Luks et al. |
| 6,395,007 B1 | 5/2002 | Bhatnagar |
| 6,398,811 B1 | 6/2002 | Mckay |
| 6,423,083 B2 | 7/2002 | Reiley et al. |
| 6,486,232 B1 | 11/2002 | Wise et al. |
| 6,506,192 B1 | 1/2003 | Gertzman et al. |
| 6,506,785 B2 | 1/2003 | Evans et al. |
| 6,520,969 B2 | 2/2003 | Lambrecht et al. |
| 6,527,773 B1 | 3/2003 | Lin et al. |
| 6,533,794 B2 | 3/2003 | Chakeres |
| 6,564,083 B2 | 5/2003 | Stevens |
| 6,607,561 B2 | 8/2003 | Brannon |
| 6,613,054 B2 | 9/2003 | Scribner |
| 6,645,213 B2 | 11/2003 | Sand et al. |
| 6,663,647 B2 | 12/2003 | Reiley et al. |
| 6,719,761 B1 | 4/2004 | Reiley |
| 6,726,691 B2 | 4/2004 | Osorio et al. |
| 6,730,124 B2 | 5/2004 | Steiner |
| 6,746,451 B2 | 6/2004 | Middleton |
| 6,767,369 B2 | 7/2004 | Boyer, II et al. |
| 6,814,736 B2 | 11/2004 | Reiley et al. |
| 6,827,720 B2 | 12/2004 | Leali |
| 6,863,672 B2 | 3/2005 | Reiley et al. |
| 6,863,899 B2 | 3/2005 | Koblish |
| 6,869,434 B2 | 3/2005 | Choi |
| 6,875,212 B2 | 4/2005 | Shaolian et al. |
| 6,887,246 B2 | 5/2005 | Bhatnagar |
| 6,899,719 B2 | 5/2005 | Reiley et al. |
| 6,917,827 B2 | 7/2005 | Kienzle et al. |
| 6,923,813 B2 | 8/2005 | Phillips et al. |
| 6,979,341 B2 | 12/2005 | Scribner et al. |
| 6,981,981 B2 | 1/2006 | Reiley et al. |
| 7,001,431 B2 | 2/2006 | Bao et al. |
| 7,029,477 B2 | 4/2006 | Grimm |
| 7,063,701 B2 | 6/2006 | Michelson |
| 7,063,702 B2 | 6/2006 | Michelson |
| 7,087,082 B2 | 8/2006 | Paul et al. |
| 7,094,239 B1 | 8/2006 | Michelson |
| 7,115,146 B2 | 10/2006 | Boyer, II et al. |
| 7,144,414 B2 | 12/2006 | Harvie et al. |
| 7,153,305 B2 | 12/2006 | Johnson et al. |
| 7,153,306 B2 | 12/2006 | Ralph et al. |
| 7,153,307 B2 | 12/2006 | Scribner |
| 7,155,306 B2 | 12/2006 | Haitin et al. |
| 7,160,305 B2 | 1/2007 | Schmieding |
| 7,226,481 B2 | 6/2007 | Kuslich |
| 7,241,303 B2 | 7/2007 | Reiss et al. |
| 7,250,055 B1 | 7/2007 | Vanderwalle |
| 7,252,671 B2 | 8/2007 | Scribner et al. |
| 7,261,716 B2 | 8/2007 | Strobel et al. |
| 7,261,720 B2 | 8/2007 | Stevens |
| 7,313,430 B2 | 12/2007 | Urquhart et al. |
| 7,399,306 B2 | 7/2008 | Reiley et al. |
| 7,410,947 B2 | 8/2008 | Rueger et al. |
| 7,448,264 B2 | 11/2008 | Boyce et al. |
| 7,458,977 B2 | 12/2008 | McGinley et al. |
| 7,468,075 B2 | 12/2008 | Lang et al. |
| 7,476,226 B2 | 1/2009 | Weikel et al. |
| 7,477,770 B2 | 1/2009 | Wehrli et al. |
| 7,485,119 B2 | 2/2009 | Thelen et al. |
| 7,488,348 B2 | 2/2009 | Truncale et al. |
| 7,491,205 B1 | 2/2009 | Michelson |
| 7,534,226 B2 | 5/2009 | Mernoe et al. |
| 7,545,964 B2 | 6/2009 | Lang et al. |
| 7,550,007 B2 | 6/2009 | Malinin |
| 7,550,011 B2 | 6/2009 | Mckay et al. |
| 7,556,295 B2 | 7/2009 | Holzheu |
| 7,559,932 B2 | 7/2009 | Truckai et al. |
| 7,575,578 B2 | 8/2009 | Wetzler et al. |
| 7,608,097 B2 | 10/2009 | Kyle |
| 7,608,098 B1 | 10/2009 | Stone et al. |
| 7,643,664 B2 | 1/2010 | Wehrli et al. |
| 7,682,378 B2 | 3/2010 | Truckai et al. |
| 7,704,256 B2 | 4/2010 | Sand et al. |
| 7,708,742 B2 | 5/2010 | Scribner |
| 7,713,273 B2 | 5/2010 | Krueer et al. |
| 7,731,720 B2 | 6/2010 | Sand et al. |
| 7,753,963 B2 | 7/2010 | Boyer, II et al. |
| 7,769,213 B2 | 8/2010 | Gregory et al. |
| 7,771,431 B2 | 8/2010 | Scribner |
| 7,789,912 B2 | 9/2010 | Manzi et al. |
| 7,811,290 B2 | 10/2010 | Rabiner |
| 7,837,733 B2 | 11/2010 | Collins et al. |
| 7,837,740 B2 | 11/2010 | Semler et al. |
| 7,840,247 B2 | 11/2010 | Liew et al. |
| 7,846,206 B2 | 12/2010 | Oglaza et al. |
| 7,879,038 B2 | 2/2011 | Reiley et al. |
| 7,879,099 B2 | 2/2011 | Zipnick |
| 7,887,543 B2 | 2/2011 | Sand et al. |
| 7,887,546 B2 | 2/2011 | Gil et al. |
| 7,896,885 B2 | 3/2011 | Miniaci et al. |
| 7,901,408 B2 | 3/2011 | Ek et al. |
| 7,901,457 B2 | 3/2011 | Truncale et al. |

(56) References Cited

U.S. PATENT DOCUMENTS

| | | |
|---|---|---|
| 7,905,924 B2 | 3/2011 | White |
| 7,914,539 B2 | 3/2011 | Stone et al. |
| 7,927,339 B2 | 4/2011 | Ralph et al. |
| 7,931,840 B2 | 4/2011 | Michelson |
| 7,938,835 B2 | 5/2011 | Boucher et al. |
| 7,959,638 B2 | 6/2011 | Osorio et al. |
| 7,985,231 B2 | 7/2011 | Sankaran |
| 8,029,511 B2 | 10/2011 | Bowman et al. |
| 8,062,364 B1 | 11/2011 | Sharkey et al. |
| 8,070,753 B2 | 12/2011 | Truckai et al. |
| 8,092,480 B2 | 1/2012 | Layne et al. |
| 8,133,226 B2 | 3/2012 | Chou et al. |
| 8,142,462 B2 | 3/2012 | Middleton |
| 8,152,813 B2 | 4/2012 | Osorio |
| 8,168,692 B2 | 5/2012 | Wenz |
| 8,187,327 B2 | 5/2012 | Edidin et al. |
| 8,246,681 B2 | 8/2012 | Osorio et al. |
| 8,608,802 B2 | 12/2013 | Bagga et al. |
| 8,617,166 B2 | 12/2013 | Hanson et al. |
| 2002/0029084 A1 | 3/2002 | Paul et al. |
| 2002/0151897 A1 | 10/2002 | Zirkle, Jr. |
| 2003/0009235 A1 | 1/2003 | Manrique et al. |
| 2003/0097135 A1 | 5/2003 | Penenberg |
| 2003/0105468 A1 | 6/2003 | Gorek |
| 2003/0138473 A1 | 7/2003 | Koblish |
| 2003/0225456 A1 | 12/2003 | Ek |
| 2004/0002759 A1 | 1/2004 | Ferree |
| 2004/0010261 A1 | 1/2004 | Hoag et al. |
| 2004/0106925 A1 | 6/2004 | Culbert |
| 2004/0127987 A1 | 7/2004 | Evans et al. |
| 2004/0167538 A1 | 8/2004 | Gerber et al. |
| 2005/0075641 A1 | 4/2005 | Singhatat et al. |
| 2005/0119219 A1 | 6/2005 | Bellini |
| 2005/0119753 A1 | 6/2005 | Mcgahan et al. |
| 2005/0149022 A1 | 7/2005 | Shaolian et al. |
| 2005/0159812 A1 | 7/2005 | Dinger, III et al. |
| 2005/0182418 A1 | 8/2005 | Boyd et al. |
| 2005/0203622 A1 | 9/2005 | Steiner et al. |
| 2005/0203623 A1 | 9/2005 | Steiner et al. |
| 2005/0256527 A1 | 11/2005 | Delfosse et al. |
| 2005/0267584 A1 | 12/2005 | Burdulis et al. |
| 2005/0288795 A1 | 12/2005 | Bagga et al. |
| 2006/0052791 A1 | 3/2006 | Hagen et al. |
| 2006/0064164 A1 | 3/2006 | Thelen |
| 2006/0084986 A1 | 4/2006 | Grinberg et al. |
| 2006/0247642 A1 | 11/2006 | Stone et al. |
| 2007/0055280 A1 | 3/2007 | Osorio et al. |
| 2007/0100462 A1 | 5/2007 | Lang et al. |
| 2007/0127987 A1 | 6/2007 | Altenbuchner |
| 2007/0276370 A1 | 11/2007 | Altarac et al. |
| 2007/0282346 A1 | 12/2007 | Scribner et al. |
| 2008/0027434 A1 | 1/2008 | Zucherman et al. |
| 2008/0039857 A1 | 2/2008 | Giersch et al. |
| 2008/0039866 A1 | 2/2008 | Stetz et al. |
| 2008/0103506 A1* | 5/2008 | Volpi et al. ............ 606/96 |
| 2008/0195115 A1 | 8/2008 | Oren et al. |
| 2008/0243127 A1 | 10/2008 | Lang et al. |
| 2008/0281331 A1 | 11/2008 | Fritzinger et al. |
| 2008/0288006 A1 | 11/2008 | Brannon |
| 2008/0306490 A1 | 12/2008 | Lakin et al. |
| 2009/0062797 A1 | 3/2009 | Huebner et al. |
| 2009/0069901 A1 | 3/2009 | Truncale et al. |
| 2009/0093813 A1 | 4/2009 | Elghazaly et al. |
| 2010/0015202 A1 | 1/2010 | Semler et al. |
| 2010/0076503 A1 | 3/2010 | Beyar |
| 2010/0145451 A1 | 6/2010 | Dee |
| 2010/0179549 A1 | 7/2010 | Keller |
| 2010/0274254 A1* | 10/2010 | Boileau et al. ............ 606/93 |
| 2011/0125156 A1 | 5/2011 | Sharkey et al. |
| 2011/0125157 A1 | 5/2011 | Sharkey et al. |
| 2011/0125160 A1 | 5/2011 | Bagga et al. |
| 2011/0125200 A1 | 5/2011 | Hanson et al. |
| 2011/0125201 A1 | 5/2011 | Hanson et al. |
| 2011/0125264 A1 | 5/2011 | Bagga et al. |
| 2011/0125265 A1 | 5/2011 | Bagga et al. |
| 2011/0125272 A1 | 5/2011 | Bagga et al. |
| 2014/0107781 A1 | 4/2014 | Bagga et al. |
| 2014/0114369 A1 | 4/2014 | Hanson et al. |

FOREIGN PATENT DOCUMENTS

| | | |
|---|---|---|
| CN | 101460105 A | 6/2009 |
| CN | 102770067 A | 11/2012 |
| CN | 102781348 A | 11/2012 |
| EP | 2501303 A1 | 9/2012 |
| EP | 2501306 A1 | 9/2012 |
| EP | 2501314 A1 | 9/2012 |
| EP | 2501342 A1 | 9/2012 |
| WO | WO-03084412 A1 | 10/2003 |
| WO | 2005/079881 A1 | 9/2005 |
| WO | WO-2008155772 A1 | 12/2008 |
| WO | WO-2011063240 A1 | 5/2011 |
| WO | WO-2011063250 A1 | 5/2011 |
| WO | WO-2011063257 A1 | 5/2011 |
| WO | WO-2011063267 A1 | 5/2011 |
| WO | WO-2011063279 A1 | 5/2011 |
| WO | WO-2011063281 A1 | 5/2011 |

OTHER PUBLICATIONS

Oct. 27, 2008 SPU Operative Report. Surgeon: Steven B Cohen, M.D.; an Anterior Cruciate Ligament (ACL) portal-creation device was repurposed for this surgery; the tibial probe was placed on the medial femoral condyle, with the tunnel guide secured proximally on the thigh; the surgeon expressed difficulty in positioning and stabilizing the guide; a cannulated pin was placed through the tunnel guide and placed distally into the medial femoral condyle; no implant was injected into the bone.

Nov. 10, 2008 SPU Operative Report. Surgeon: Steven B Cohen, M.D.; Treatment of the central medial tibial plateau; a guide pin was inserted into the medial tibial plateau; an endo button drill bit was used to expand the drill hole; One cubic centimeter (cc) of cement was inserted into the bone; a second drill hole was made from below, and a second cc was inserted into the bone.

"U.S. Appl. No. 12/950,230, Non Final Office Action mailed Jul. 17, 2014", 10 pgs.

"U.S. Appl. No. 12/950,355, Non Final Office Action mailed Jul. 29, 2014", 9 pgs.

"U.S. Appl. No. 14/143,883, Non Final Office Action mailed Aug. 4, 2014", 6 pgs.

"Chinese Application Serial No. 201080052569.2, Office Action mailed Apr. 25, 2014", w/English Translation, 17 pgs.

"U.S. Appl. No. 12/950,061, Final Office Action mailed Jul. 15, 2013", 7 pgs.

"U.S. Appl. No. 12/950,061, Non Final Office Action mailed Feb. 7, 2013", 7 pgs.

"U.S. Appl. No. 12/950,061, Notice of Allowance mailed Oct. 1, 2013", 6 pgs.

"U.S. Appl. No. 12/950,061, Preliminary Amendment filed Feb. 8, 2011", 3 pgs.

"U.S. Appl. No. 12/950,061, Response filed Jun. 7, 2013 to Non Final Office Action mailed Feb. 7, 2013", 14 pgs.

"U.S. Appl. No. 12/950,061, Response filed Sep. 16, 2013 to Final Office Action mailed Jul. 15, 2013", 13 pgs.

"U.S. Appl. No. 12/950,097, Final Office Action mailed Feb. 10, 2013", 6 pgs.

"U.S. Appl. No. 12/950,097, Non Final Office Action mailed Feb. 15, 2013", 8 pgs.

"U.S. Appl. No. 12/950,097, Non Final Office Action mailed Aug. 6, 2013", 6 pgs.

"U.S. Appl. No. 12/950,097, Notice of Allowance mailed Apr. 2, 2014", 5 pgs.

"U.S. Appl. No. 12/950,097, Preliminary Amendment filed Feb. 7, 2011", 3 pgs.

"U.S. Appl. No. 12/950,097, Response filed Jun. 17, 2013 to Non Final Office Action mailed Feb. 15, 2013", 15 pgs.

"U.S. Appl. No. 12/950,097, Response filed Nov. 6, 2013 to Non Final Office Action mailed Aug. 6, 2013", 14 pgs.

"U.S. Appl. No. 12/950,097, Response filed Mar. 10, 2014 to Final Office Action mailed Dec. 10, 2013", 13 pgs.

"U.S. Appl. No. 12/950,114, Final Office Action mailed Jul. 15, 2013", 6 pgs.

(56) References Cited

OTHER PUBLICATIONS

"U.S. Appl. No. 12/950,114, Non Final Office Action mailed Feb. 6, 2014", 6 pgs.
"U.S. Appl. No. 12/950,114, Non Final Office Action mailed Mar. 7, 2013", 6 pgs.
"U.S. Appl. No. 12/950,114, Preliminary Amendment filed Feb. 8, 2011", 3 pgs.
"U.S. Appl. No. 12/950,114, Response filed Jun. 7, 2013 to Non Final Office Action mailed Mar. 7, 2013", 8 pgs.
"U.S. Appl. No. 12/950,114, Response filed Sep. 16, 2013 to Final Office Action mailed Jul. 15, 2013", 8 pgs.
"U.S. Appl. No. 12/950,114, Response filed May 6, 2014 to Non-Final Office Action dated Feb. 6, 2014", 7 pgs.
"U.S. Appl. No. 12/950,183, Examiner Interview Summary mailed Feb. 13, 2014", 3 pgs.
"U.S. Appl. No. 12/950,183, Final Office Action mailed Oct. 30, 2012", 16 pgs.
"U.S. Appl. No. 12/950,183, Non Final Office Action mailed May 29, 2012", 10 pgs.
"U.S. Appl. No. 12/950,183, Non Final Office Action mailed Oct. 11, 2013", 12 pgs.
"U.S. Appl. No. 12/950,183, Notice of Allowance mailed Feb. 19, 2014", 5 pgs.
"U.S. Appl. No. 12/950,183, Preliminary Amendment filed Feb. 8, 2011", 4 pgs.
"U.S. Appl. No. 12/950,183, Response filed Jan. 13, 2014 to Non Final Office Action mailed Oct. 11, 2013", 11 pgs.
"U.S. Appl. No. 12/950,183, Response filed Apr. 30, 2013 to Final Office Action mailed Oct. 30, 2012", 11 pgs.
"U.S. Appl. No. 12/950,183, Response filed May 11, 2012 to Restriction Requirement mailed Apr. 13, 2012", 2 pgs.
"U.S. Appl. No. 12/950,183, Response filed Aug. 28, 2012 to Non Final Office Action mailed May 29, 2012", 10 pgs.
"U.S. Appl. No. 12/950,183, Restriction Requirement mailed Apr. 13, 2012", 8 pgs.
"U.S. Appl. No. 12/950,183, Supplemental Amendment filed Feb. 7, 2014", 8 pgs.
"U.S. Appl. No. 12/950,230, Final Office Action mailed Jan. 11, 2013", 10 pgs.
"U.S. Appl. No. 12/950,230, Non Final Office Action mailed Aug. 2, 2012", 9 pgs.
"U.S. Appl. No. 12/950,230, Preliminary Amendment filed Feb. 8, 2011", 3 pgs.
"U.S. Appl. No. 12/950,230, Response filed Apr. 11, 2013 to Final Office Action mailed Jan. 11, 2013", 10 pgs.
"U.S. Appl. No. 12/950,230, Response filed Nov. 2, 2012 to Non Final Office Action mailed Aug. 2, 2012", 8 pgs.
"U.S. Appl. No. 12/950,273, Final Office Action mailed Nov. 6, 2012", 9 pgs.
"U.S. Appl. No. 12/950,273, Non Final Office Action mailed Apr. 13, 2012", 15 pgs.
"U.S. Appl. No. 12/950,273, Non Final Office Action mailed Apr. 25, 2014", 12 pgs.
"U.S. Appl. No. 12/950,273, Preliminary Amendment filed Feb. 8, 2011", 3 pgs.
"U.S. Appl. No. 12/950,273, Response filed Mar. 6, 2013 to Final Office Action mailed Nov. 6, 2012", 10 pgs.
"U.S. Appl. No. 12/950,273, Response filed Jul. 12, 2012 to Non Final Office Action mailed Apr. 13, 2012", 12 pgs.
"U.S. Appl. No. 12/950,306, Final Office Action mailed Nov. 26, 2012", 9 pgs.
"U.S. Appl. No. 12/950,306, Non Final Office Action mailed Jun. 14, 2012", 11 pgs.
"U.S. Appl. No. 12/950,306, Notice of Allowance mailed May 28, 2013", 9 pgs.
"U.S. Appl. No. 12/950,306, Notice of Allowance mailed Aug. 13, 2013", 9 pgs.
"U.S. Appl. No. 12/950,306, Preliminary Amendment filed Feb. 8, 2011", 7 pgs.
"U.S. Appl. No. 12/950,306, Response filed Apr. 30, 2013 to Final Office Action mailed Nov. 26, 2012", 15 pgs.
"U.S. Appl. No. 12/950,306, Response filed Sep. 13, 2012 to Non Final Office Action mailed Jun. 14, 2012", 11 pgs.
"U.S. Appl. No. 12/950,355, Final Office Action mailed Mar. 12, 2013", 15 pgs.
"U.S. Appl. No. 12/950,355, Non Final Office Action mailed Aug. 13, 2012", 16 pgs.
"U.S. Appl. No. 12/950,355, Response filed Jan. 14, 2013 to Non Final Office Action mailed Aug. 13, 2012", 17 pgs.
"U.S. Appl. No. 12/950,355, Response filed Jul. 12, 2013 to Final Office Action mailed Mar. 12, 2013", 20 pgs.
"Chinese Application Serial No. 201080052578.1, Office Action mailed Apr. 1, 2014", w/English Translation, 11 pgs.
"Chinese Application Serial No. 201080052580.9, Office Action mailed Apr. 3, 2014", w/English Translation, 13 pgs.
"Chinese Application Serial No. 201080052583.2, Office Action mailed Mar. 14, 2014", w/English Translation, 9 pgs.
"European Application Serial No. 10832277.7, Office Action mailed Jun. 27, 2012", 2 pgs.
"European Application Serial No. 10832285.0, Office Action mailed Jun. 27, 2012", 2 pgs.
"International Application Serial No. 01/24/2011, International Preliminary Report on Patentability mailed May 22, 2012", 9 pgs.
"International Application Serial No. PCT/US2010/057426, International Search Report and Written Opinion mailed Jan. 24, 2011", 10 pgs.
"International Application Serial No. PCT/US2010/057440, International Preliminary Report on Patentability mailed May 22, 2012", 7 pgs.
"International Application Serial No. PCT/US2010/057440, International Search Report and Written Opinion mailed Feb. 7, 2011", 8 pgs.
"International Application Serial No. PCT/US2010/057456, International Preliminary Report on Patentability mailed May 22, 2012", 6 pgs.
"International Application Serial No. PCT/US2010/057456, International Search Report and Written Opinion mailed Jan. 14, 2011", 7 pgs.
"International Application Serial No. PCT/US2010/057471, International Preliminary Report on Patentability mailed May 31, 2012", 7 pgs.
"International Application Serial No. PCT/US2010/057471, International Search Report mailed Jan. 18, 2011", 2 pgs.
"International Application Serial No. PCT/US2010/057471, Written Opinion mailed Jan. 18, 2011", 5 ogs.
"International Application Serial No. PCT/US2010/057475, International Preliminary Report on Patentability mailed May 22, 2012", 6 pgs.
"International Application Serial No. PCT/US2010/057475, International Search Report mailed Jan. 18, 2011", 8 pgs.
"International Application Serial No. PCT/US2010/057475, Written Opinion mailed Jan. 18, 2011", 5 pgs.
"International Application Serial No. PCT/US2010/057483, International Preliminary Report on Patentability mailed May 22, 2012", 6 pgs.
"International Application Serial No. PCT/US2010/057483, International Search Report and Written Opinion mailed Feb. 2, 2011", 7 pgs.
"International Application Serial No. PCT/US2010/057498, International Preliminary Report on Patentability mailed May 22, 2012", 5 pgs.
"International Application Serial No. PCT/US2010/057498, International Search Report mailed Jan. 24, 2011", 2 pgs.
"International Application Serial No. PCT/US2010/057498, Written Opinion mailed Jan. 24, 2011", 4 pgs.
"International Application Serial No. PCT/US2010/057500, International Preliminary Report on Patentability mailed May 31, 2012", 8 pgs.
"International Application Serial No. PCT/US2010/057500, International Search Report mailed Jan. 27, 2011", 2 pgs.
"International Application Serial No. PCT/US2010/057500, Written Opinion mailed Jan. 27, 2011", 6 pgs.

* cited by examiner

INSTRUMENTS FOR A VARIABLE ANGLE APPROACH TO A JOINT

CROSS-REFERENCE TO RELATED APPLICATIONS

This application claims priority to U.S. Provisional No. 61/310,897, filed Mar. 5, 2010, and entitled "INSTRUMENTS FOR VARIABLE ANGLE APPROACH TO JOINT REPAIR AND METHODS OF USE," U.S. Provisional No. 61/311,152, filed Mar. 5, 2010, and entitled "INSTRUMENTS FOR REPAIRING AN UPPER BONE OF A JOINT AND METHODS OF USE," and U.S. Provisional No. 61/263,170 filed Nov. 20, 2009, and entitled "METHOD FOR TREATING JOINT PAIN AND ASSOCIATED INSTRUMENTS," all of which are herein incorporated by reference in their entirety.

This application also related to co-pending and co-owned U.S. patent application Ser. No. 12/950,355, filed Nov. 19, 2010 and entitled "SUBCHONDRAL TREATMENT OF JOINT PAIN," the content of which is herein incorporated in its entirety by reference.

FIELD

The present invention relates to devices and tools for the surgical treatment of joints, and more particularly to instruments that allow various angular approaches to the surgical repair and treatment of bone tissue at these joints and associated methods of use.

BACKGROUND

Human joints, in particular the knee, hip and spine, are susceptible to degeneration from disease, trauma, and long-term repetitive use that eventually lead to pain. Knee pain, for example, is the impetus for a wide majority of medical treatments and associated medical costs. The most popular theory arising from the medical community is that knee pain results from bone-on-bone contact or inadequate cartilage cushioning. These conditions are believed to frequently result from the progression of osteoarthritis, which is measured in terms of narrowing of the joint space. Therefore, the severity of osteoarthritis is believed to be an indicator or precursor to joint pain. Most surgeons and medical practitioners thus base their treatments for pain relief on this theory. For example, the typical treatment is to administer pain medication, or more drastically, to perform some type of joint resurfacing or joint replacement surgery.

However, the severity of osteoarthritis, especially in the knee, has been found to correlate poorly with the incidence and magnitude of knee pain. Because of this, surgeons and medical practitioners have struggled to deliver consistent, reliable pain relief to patients especially if preservation of the joint is desired.

Whether by external physical force, disease, or the natural aging process, structural damage to bone can cause injury, trauma, degeneration or erosion of otherwise healthy tissue. The resultant damage can be characterized as a bone defect that can take the form of a fissure, fracture, lesion, edema, tumor, or sclerotic hardening, for example. Particularly in joints, the damage may not be limited to a bone defect, and may also include cartilage loss (especially articular cartilage), tendon damage, and inflammation in the surrounding area.

Patients most often seek treatment because of pain and deterioration of quality of life attributed to the osteoarthritis. The goal of surgical and non-surgical treatments for osteoarthritis is to reduce or eliminate pain and restore joint function. Both non-surgical and surgical treatments are currently available for joint repair.

Non-surgical treatments include weight loss (for the overweight patient), activity modification (low impact exercise), quadriceps strengthening, patellar taping, analgesic and anti-inflammatory medications, and with corticosteroid and/or viscosupplements. Typically, non-surgical treatments, usually involving pharmacological intervention such as the administration of non-steroidal anti-inflammatory drugs or injection of hyaluronic acid-based products, are initially administered to patients experiencing relatively less severe pain or joint complications. However, when non-surgical treatments prove ineffective, or for patients with severe pain or bone injury, surgical intervention is often necessary.

Surgical options include arthroscopic partial meniscectomy and loose body removal. Most surgical treatments conventionally employ mechanical fixation devices such as screws, plates, staples, rods, sutures, and the like are commonly used to repair damaged bone. These fixation devices can be implanted at, or around, the damaged region to stabilize or immobilize the weakened area, in order to promote healing and provide support. Injectable or fillable hardening materials such as bone cements, bone void fillers, or bone substitute materials are also commonly used to stabilize bone defects.

High tibial osteotomy (HTO) or total knee arthroplasty (TKA) is often recommended for patients with severe pain associated with osteoarthritis, especially when other non-invasive options have failed. Both procedures have been shown to be effective in treating knee pain associated with osteoarthritis.

However, patients only elect HTO or TKA with reluctance. Both HTO and TKA are major surgical interventions and may be associated with severe complications. HTO is a painful procedure that may require a long recovery. TKA patients often also report the replaced knee lacks a "natural feel" and have functional limitations. Moreover, both HTO and TKA have limited durability. Accordingly, it would be desirable to provide a medical procedure that addresses the pain associated with osteoarthritis and provides an alternative to a HTO or TKA procedure.

One of the difficulties of currently available surgical access devices and insertion tools is the ability to target a specific area of the bone to be treated, in a fast, accurate, easy and repeatable manner. Presently, in order to treat or repair a bone defect at a joint, the surgeon often has to take multiple steps using multiple surgical tools in order to access, locate, and treat the target defect site. Even so, the surgeon does not have a reliable instrument or system that would allow him to repeatedly target the same site and from multiple angles or locations outside the body. In order to perform repeated or multiple procedures in the same defect location with the currently available tools, additional and unnecessary time in the operating room would be required, as well as an increased risk for complications since numerous instruments and maneuvers are at play.

Accordingly, it is desirable to provide instruments that allow fast, easy, precise and repeatable surgical access to the target site, or the bone defect, to be treated. It is further desirable to provide instruments that enable the user to easily and accurately target the defect from multiple angles or locations outside the body.

SUMMARY

The present disclosure provides instruments and associated methods for the surgical repair and treatment of bone tissue, particularly of bone tissue at joints. More specifically, the instruments of the present disclosure allow various angular approaches to target an area local to a bone defect in a joint. The present disclosure also provides instruments that allow fast, easy, precise and repeatable surgical targeting of a defect in a lower or upper bone of a joint, and even more specifically of a defect in a tibia or femur of a knee joint near the contact surface.

In one embodiment, a positioning instrument is provided for controlled delivery of a device or bone substitute material to a target site of the bone tissue being treated. The positioning instrument may comprise a main body extending at one end into an indicator probe for visual determination of a target site of a bone to be treated, and at an opposite end into a handle. A rail extends from the main body. The instrument also includes an alignment guide having a device portal for insertion of a device therethrough, the alignment guide being detachable and movable along a length of the rail. The device portal is configured to provide accurate and controlled delivery of the device to the target site indicated by the indicator probe. The device may comprise an implant insertion tool, an injection catheter, a cavity creation tool such as a bone drill, for example, or the device may be an implantable device.

In another embodiment, a method for treating a bone defect at a joint is provided. The method may include the steps of providing a positioning instrument for controlled delivery of a device or a bone substitute material to a target site in the bone tissue, the positioning instrument comprising a main body extending at one end into an indicator probe for visual determination of a target site of a bone to be treated, and at an opposite end into a handle, a rail extending from the main body, and an alignment guide having a device portal for insertion of a device therethrough, the alignment guide being detachable and movable along a length of the rail, and introducing a device through the device portal of the alignment guide and to the target site.

It is to be understood that both the foregoing general description and the following detailed description are exemplary and explanatory only and are not restrictive of the disclosure. Additional features of the disclosure will be set forth in part in the description which follows or may be learned by practice of the disclosure.

BRIEF DESCRIPTION OF THE DRAWINGS

The accompanying drawings, which are incorporated in and constitute a part of this specification, illustrate several embodiments of the disclosure and together with the description, serve to explain the principles of the disclosure.

DESCRIPTION OF THE EMBODIMENTS

Figure 1A:
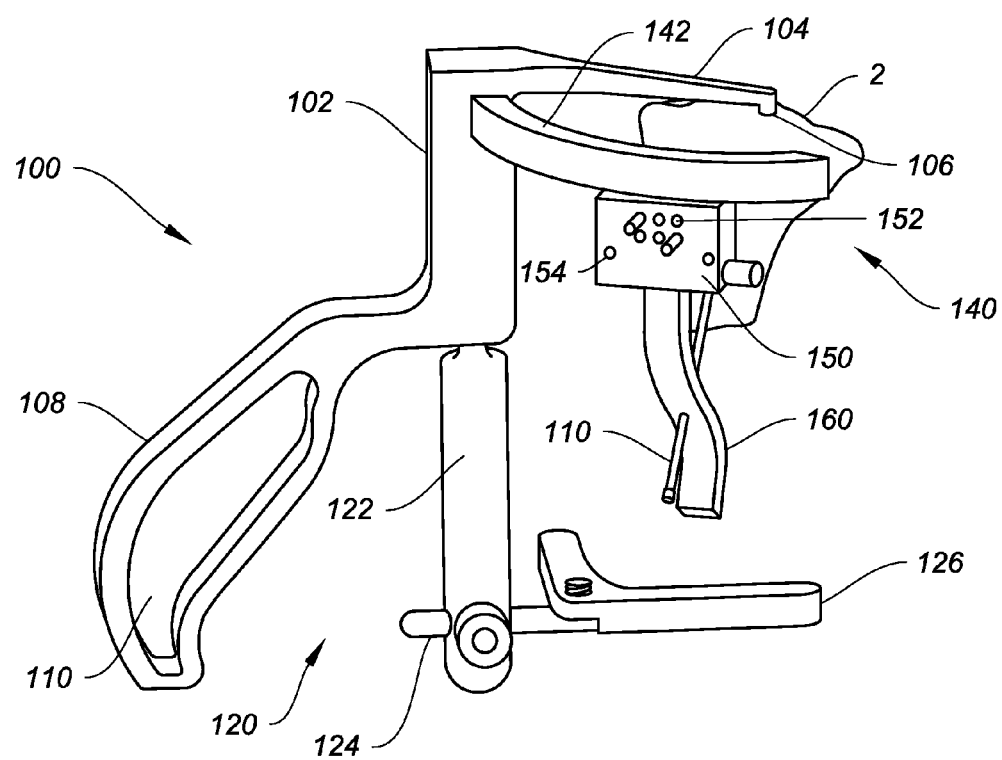
FIG. 1A is a side view of an exemplary embodiment of a positioning instrument of the present invention shown in use with a partial bone.

The present disclosure provides a methodology, devices and instruments for diagnosing and treating joint pain to restore natural joint function and preserving, as much as possible, the joint's articular and cartilage surface. Treatments through the joint that violate the articular and cartilage surface often weaken the bone and have unpredictable results. Rather than focusing on treatment of pain through the joint, the embodiments diagnose and treat pain at its source in the subchondral region of a bone of a joint to relieve the pain. Applicants have discovered that pain associated with joints, especially osteoarthritic joints, can be correlated to bone defects or changes at the subchondral level rather than, for example, the severity of osteoarthritic progression or defects at the articular surface level. In particular, bone defects, such as bone marrow lesions, edema, fissures, fractures, hardened bone, etc. near the joint surface lead to a mechanical disadvantage and abnormal stress distribution in the periarticular bone, which may cause inflammation and generate pain. By altering the makeup of the periarticular bone (which may or may not be sclerotic) in relation to the surrounding region, it is possible to change the structural integrity of the affected bone and restore normal healing function, thus leading to a resolution of the inflammation surrounding the defect.

Applicants have discovered that treatment of the bone by mechanical and biological means to restore the normal physiologic stress distribution, and restore the healing balance of the bone tissue at the subchondral level, is a more effective way of treating pain than conventional techniques. That is, treatment can be effectively achieved by mechanically strengthening or stabilizing the defect, and biologically initiating or stimulating a healing response to the defect. Accordingly, the present disclosure provides methods, devices, and systems for a subchondral procedure. This procedure and its associated devices, instruments, etc. are also marketed under the registered trademark name of SUBCHONDRO-PLASTY™. The SUBCHONDROPLASTY™ procedure is a response to a desire for an alternative to patients facing partial or total knee replacement.

In general, the SUBCHONDROPLASTY™ or SCP™ technique is intended to both strengthen the bone and stimulate the bone. In SCP™, bone fractures or non-unions are stabilized, integrated or healed, which results in reduction of a bone defect, such as a bone marrow lesion or edema. In addition, SCP™ restores or alters the distribution of forces in a joint to thereby relieve pain. SCP™ can be performed arthroscopically or percutaneously to treat pain by stabilizing chronic stress fracture, resolving any chronic bone marrow lesion or edema, and preserving, as much as possible, the articular surfaces of the joint. SUBCHONDROPLASTY™ generally comprises evaluating a joint, for example, by taking an image of the joint, detecting the presence of one or more subchondral defects, diagnosing which of these subchondral defects is the source of pain, and determining an extent of treatment for the subchondral defect. The present technique is particularly suited for treating chronic defects or injuries, where the patient's natural healing response has not resolved the defect. It should be noted, however, that the technique is equally applicable to treatment of defects in the subchondral region of bone where the defect is due to an acute injury or from other violations. The present disclosure provides several exemplary treatment modalities for SCP™ for the different extents of treatment needed. Accordingly, a medical practitioner may elect to use the techniques and devices described herein to subchondrally treat any number of bone defects as he deems appropriate.

In some embodiments, detection and identification of the relevant bone marrow lesion or bone marrow edema (BML or BME) can be achieved by imaging, e.g., magnetic resonance imaging (MRI), X-ray, manual palpation, chemical or biological assay, and the like. A T1-weighted MRI can be used to detect sclerotic bone, for example. Another example is that a T2-weighted MRI can be used to detect lesions, edemas, and cysts. X-ray imaging may be suitable for early-stage as well as end-stage arthritis. From the imaging, certain defects may be identified as the source of pain. In general, defects that are associated with chronic injury and chronic deficit of healing are differentiated from defects that result, e.g., from diminished bone density. SCP™ treatments are appropriate for a BML or BME that may be characterized as a bone defect that is chronically unable to heal (or remodel) itself, which may cause a non-union of the bone, stress or insufficiency fractures, and perceptible pain. Factors considered may include, among other things, the nature of the defect, size of the defect, location of the defect, etc. For example, bone defects at the edge near the articular surface or periphery of a joint may be often considered eligible for treatment due to edge-loading effects as well as the likelihood of bone hardening at these locations. A bone defect caused by an acute injury would generally be able to heal itself through the patient's own natural healing process. However, in such situations where the bone defect is due to an acute injury and either the defect does not heal on its own, or the medical practitioner decides that the present technique is appropriate, SCP™ treatments can be administered on acute stress fractures, BML or BME, or other subchondral defects, as previously mentioned.

According to the embodiments, the SCP™ treatment may continue after surgery. In particular, the patient may be monitored for a change in pain scores, or positive change in function. For example, patients are also checked to see when they are able to perform full weight-bearing activity and when they can return to normal activity. Of note, if needed, the SCP™ procedure can be completely reversed in the event that a patient requires or desires a joint replacement or other type of procedure. The SCP™ treatment may also be performed in conjunction with other procedures, such as cartilage resurfacing, regeneration or replacement, if desired.

The present disclosure provides a number of treatment modalities, and associated devices, instruments and related methods of use for performing SUBCHONDROPLASTY™. These treatment modalities may be used alone or in combination.

In one treatment modality, the subchondral bone in the region of the bone marrow lesion or defect can be strengthened by introduction of a hardening material, such as a bone substitute, at the site. The bone substitute may be an injectable calcium phosphate ensconced in an optimized carrier material. In SCP™, the injected material may also serve as a bone stimulator that reinvigorates the desired acute bone healing activity.

For example, polymethylmethacrylate (PMMA) or calcium phosphate (CaP) cement injections can be made at the defect site. PMMA injection may increase the mechanical strength of the bone, allowing it to withstand greater mechanical stresses. CaP cement injection may also increase the mechanical strength of the bone, while also stimulating the localized region for bone fracture repair. In one embodiment, the injection can be made parallel to the joint surface. In another embodiment, the injection can be made at an angle to the joint surface. In yet another embodiment, the injection can be made below a bone marrow lesion.

In another treatment modality, the subchondral bone region can be stimulated to trigger or improve the body's natural healing process. For example, in one embodiment of this treatment modality, one or more small holes may be drilled at the region of the defect to increase stimulation (e.g., blood flow, cellular turnover, etc.) and initiate a healing response leading to bone repair. In another embodiment, after holes are drilled an osteogenic, osteoinductive, or osteoconductive agent may be introduced to the site. Bone graft material, for example, may be used to fill the hole. This treatment modality may create a better load-supporting environment leading to long term healing. Electrical or heat stimulation may also be employed to stimulate the healing process of a chronically injured bone. Chemical, biochemical and/or biological stimulation may also be employed in SCP™. For instance, stimulation of bone tissue in SCP™ may be enhanced via the use of cytokines and other cell signaling agents to trigger osteogenesis, chondrogenesis, and/or angiogenesis to perhaps reverse progression of osteoarthritis.

In yet another treatment modality, an implantable device may be implanted into the subchondral bone to provide mechanical support to the damaged or affected bone region, such as where an insufficiency fracture or stress fracture has occurred. The implant may help create a better load distribution in the subchondral region. In the knees, the implant may support tibio-femoral compressive loads. In addition, the implant may mechanically integrate sclerotic bone with the surrounding healthy bone tissue. The implant may be placed in cancellous bone, through sclerotic bone, or under sclerotic bone at the affected bone region. The implant may also be configured as a bi-cortical bone implant. In one embodiment, one side of the implant can be anchored to the peripheral cortex to create a cantilever beam support (i.e., a portion of the implant is inserted into bone but the second end stays outside or near the outer surface of the bone). The implant may be inserted using a guide wire. In one example, the implant may be inserted over a guide wire. In another example, the implant may be delivered through a guide instrument.

The implant may further be augmented with a PMMA or CaP cement injection, other biologic agent, or an osteoconductive, osteoinductive and/or osteogenic agent. The augmentation material may be introduced through the implant, around the implant, and/or apart from the implant but at the affected bone region, such as into the lower region of a bone marrow lesion or below the lesion. For example, the implant may act as a portal to inject the augmentation material into the subchondral bone region.

While each of the above-mentioned treatment modalities may be administered independent of one another, it is contemplated that any combination of these modalities may be applied together and in any order so desired, depending on the severity or stage of development of the bone defect(s). Accordingly, the present disclosure also provides suitable implantable fixation devices for the surgical treatment of these altered bone regions or bone defects, especially at the subchondral level. Applicants have also discovered devices and instruments that can be used in combination with cements or hardening materials commonly used to repair damaged bone by their introduction into or near the site of damage, either to create a binding agent, cellular scaffold or mechanical scaffold for immobilization, regeneration or remodeling of the bone tissue.

In general, the embodiments relate to instruments and associated methods for the surgical treatment of a joint, and particularly to a bone defect at that joint region. More specifically, the embodiments relate to instruments that allow variable angle approaches to the surgical repair and treatment of bone tissue at these joints and associated methods of use. Even more specifically, in one embodiment the instruments and associated methods for use are suitable for the repair of a tibial bone of a knee joint. In another embodiment, the instruments of the present disclosure allow fast, easy, precise and repeatable surgical targeting of a defect in an upper bone of a joint, and even more specifically of a defect in a femur near the contact surface.

In a healthy joint such as a tibio-femoral joint, the compressive load between the contact bones (i.e., the femur and the tibia) is properly distributed, thus keeping the contact stresses in the cartilage to a reasonably low level. As the cartilage starts to wear out locally, the tibio-femoral contact area reduces and starts to get localized at the site of the cartilage defect. The localization of the stresses may also occur due to varus or valgus deformity. Sometimes, the condition may occur because of osteoporosis, where bone becomes weak and is no longer able to support normal loads. This condition leads to higher localized contact stresses in the cartilage, and the subchondral region below the cartilage. Once the stresses reach beyond a certain threshold level, it leads to defects like bone marrow lesions and edema, and perhaps generates knee pain. If the problem persists, the high contact stresses can lead to sclerotic bone formation as well. The presence of sclerotic bone can compromise vascularization of the local area, and also create a mechanical mismatch in the bone tissue. This mismatch may start to expedite degeneration of all parts of the joint leading to increased levels of osteoarthritis.

With this understanding, applicants have discovered that pain associated with osteoarthritic joints can be correlated to bone defects or changes at the subchondral level. In particular, bone defects, such as bone marrow lesions, edema, fissures, fractures, etc. near the joint surface lead to abnormal stress distribution in the periarticular bone, which may or may not cause inflammation and generate pain. By altering the makeup of the periarticular bone (which may or may not be sclerotic) in relation to the surrounding region, it is possible to change the structural integrity of the affected bone, leading to a resolution of the inflammation. Applicants have discovered that treatment of the bone in an effort to alter the structural makeup of the affected periarticular bone leads to reduced inflammation and pain. Over time, normal physiologic stress distribution can be achieved, and mechanical congruity restored, thereby resulting in healing of the inflammation and reduction or elimination of pain.

As previously mentioned, there is a need for surgical instruments that allow fast, easy, precise and repeatable surgical access to the target site, or the bone defect, to be treated. Applicants have discovered instruments that are particularly suitable for accessing certain areas of the bone within the range of about 2-15 mm from the bone surface, and more commonly about 5-10 mm from the bone surface, such as the articular surface or the subchondral bone area, and therefore require more precise defect location features. These instruments are also particularly suited to aid in the insertion of tools, bone substitute material, devices, implants, etc. in a predetermined angular orientation with respect to the top surface of the bone to be treated (e.g., in a parallel orientation). Accordingly, the present invention provides suitable instruments and associated methods for the surgical treatment of these bone defects, especially at the subchondral level near sclerotic bone.

Figure 1B:
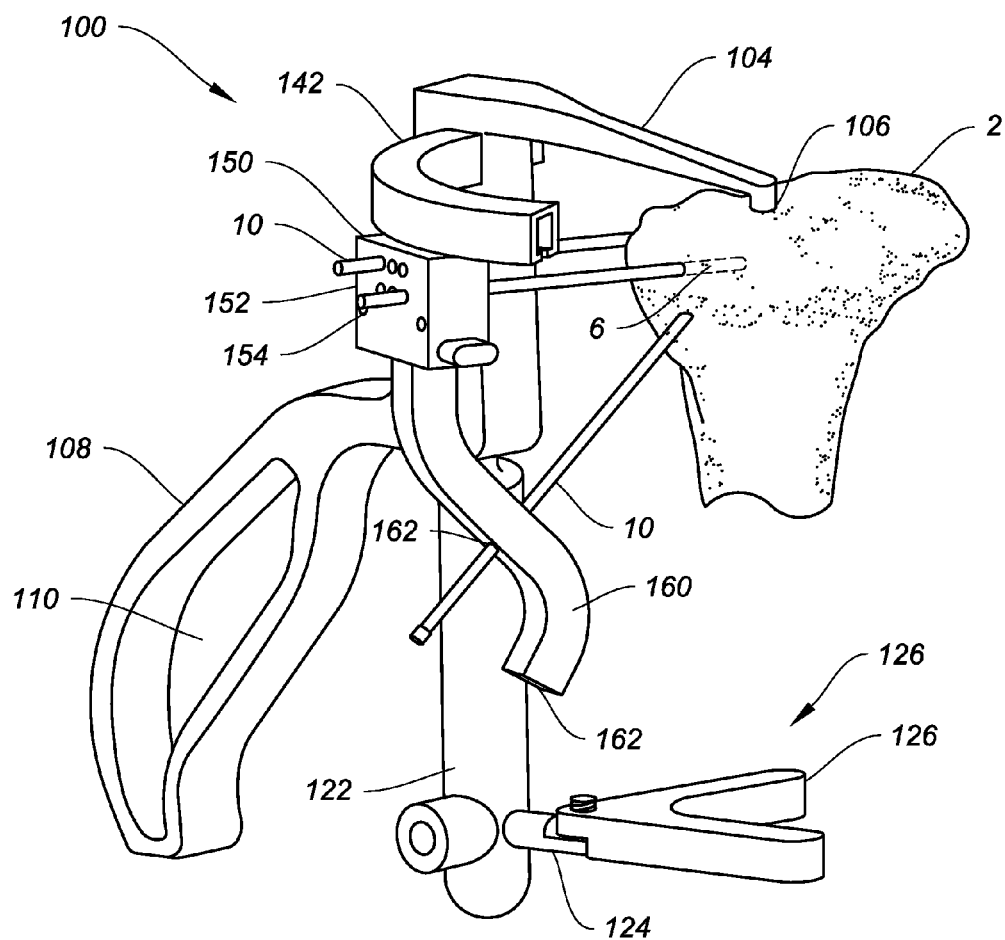
FIG. 1B is a perspective view of the positioning instrument of FIG. 1A shown in use with a partial bone.

Turning now to the drawings, FIGS. 1A and 1B show an exemplary embodiment of a positioning instrument 100 of the present disclosure. The positioning instrument 100 enables repeatable, controlled delivery of a device to a target area 6 in the bone 2. As shown, the device may be a pin 10. However, the term "device" is used herein to refer generally to any number of implantable devices, materials (such as bone substitute materials) and instruments suitable for bone treatment and/or repair. As will be described in more detail below, the device may be an implantable device, an insertion tool, a drill bit, an injection needle, a catheter, or any other surgical instrument. Exemplary implantable devices are disclosed in co-pending and co-owned U.S. patent application Ser. No. 12/950,306, filed Nov. 19, 2010 and entitled "IMPLANTABLE DEVICES FOR SUBCHONDRAL TREATMENT OF JOINT PAIN," U.S. patent application Ser. No. 12/950,273, filed Nov. 19, 2010 and entitled "IMPLANTABLE DEVICES FOR SUBCHONDRAL TREATMENT OF JOINT PAIN," and U.S. patent application Ser. No. 12/950,183, filed Nov. 19, 2010 and entitled "BONE-DERIVED IMPLANTABLE DEVICES FOR SUBCHONDRAL TREATMENT OF JOINT PAIN," the contents of which are herein incorporated in their entirety by reference. Accordingly, the positioning instrument 100 may be used to provide quick, easy, accurate and repeatable targeting of a specific bone defect for a number of instruments or implants that can perform any variety of treatment functions.

The positioning instrument 100 is configured to provide simple, repeatable targeting of a local target area 6 at or near a bone defect in a bone of a joint for percutaneous treatment of the defect. In addition, the positioning instrument 100 allows targeting of a target area 6 from various angles, or locations, outside the bone 2. In the drawings and embodiments described, the bone may be a tibia 2 of a knee joint, for example. However, it is understood that the bone may be any other kind of joint bone.

As FIGS. 1A and 1B illustrate, the positioning instrument 100 may comprise a main body 102 from which an indicator probe 104 extends. In one embodiment, the probe 104 may extend at an angle to a transverse plane of the bone. The angle could be in the range of about 1 to 15 degrees, more preferably about 2 to 10 degrees, and even more preferably about 3 to 7 degrees. In one example for use with a tibia 2, the probe 104 may be configured to extend at an angle of about 7 degrees to a transverse plane of the tibial plateau. This slight angle enables the probe 104 to be oriented parallel to the tibial plateau (which has this inherent slope), thereby allowing the user to have instrumentation that better matches the natural contours of the bone to be treated and which allows for the correct angular access to the target site. Accordingly, the angular orientation of the probe 104 allows the user a greater angular opening to access the bone clear of ligament and other surrounding soft tissue, and prevents inadvertent angular insertion of any instruments or devices through cartilage or other unintended bone or soft tissue, causing damage to the joint.

The indicator probe 104 may include on its underside at the terminal end a knob 106 for placement against a bone surface. At an opposite end the main body 102 extends into a handle 108. The handle 108 may be configured with a cutout portion 110 for gripping the instrument 100. Tool-receiving holes 112 may be provided on the main body 102, as shown in FIGS. 2A and 2B, for receiving a tool such as a pin 10 to further secure the positioning instrument 100 against the bone 2.

Figure 3A:
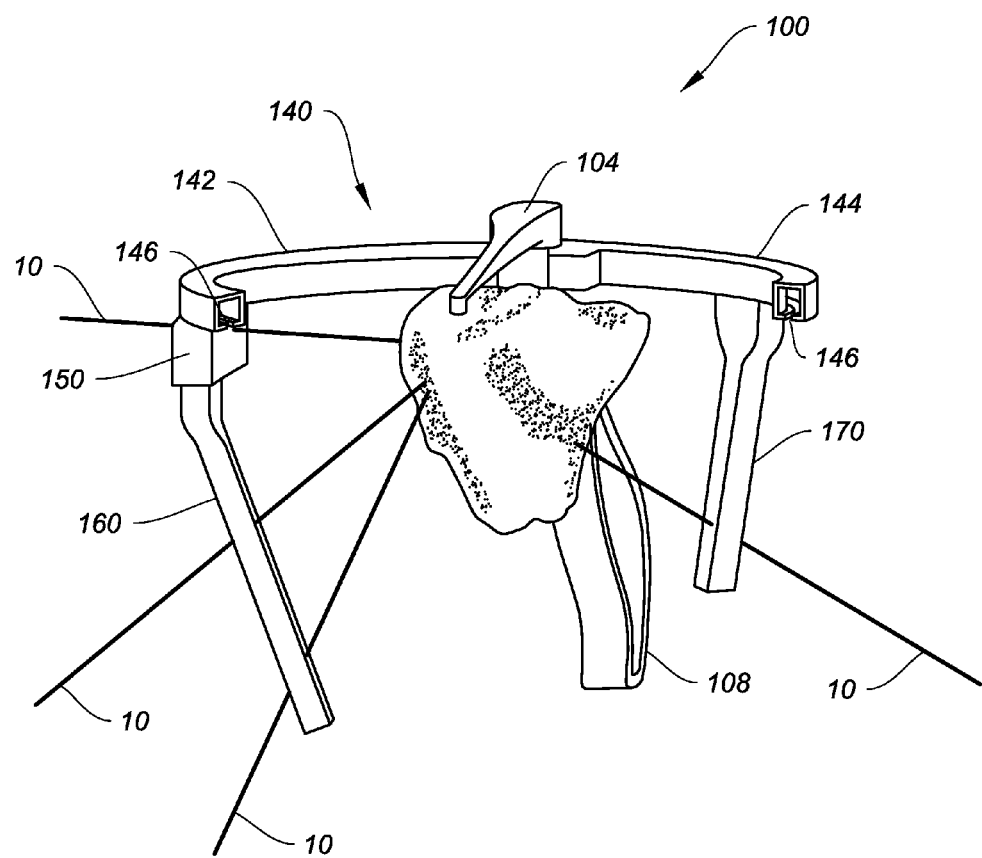
FIG. 3A is a perspective view of another exemplary embodiment of a positioning instrument of the present invention in use with a partial bone.
Figure 3B:
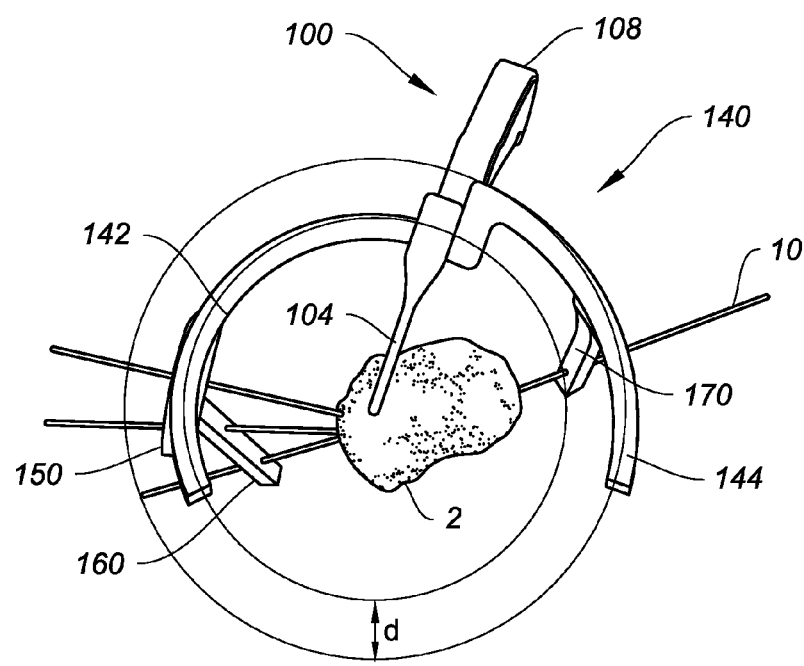
FIG. 3B is a top-down view of the positioning instrument of FIG. 3A and partial bone.

A stabilizer component 120 may optionally be provided for use with the positioning instrument 100. The stabilizer component 120 may be detachable, and include a shaft 122 that can be quickly and easily attached or removed from the main body 102 of the positioning instrument 100. It is contemplated that the shaft 122 may be configured to be adjustable in length relative to the main body 102 to accommodate different sized patients. A stem 124 may extend from the shaft 122, as shown in FIG. 1A. The stem 124 may be configured to be angularly adjustable relative to the shaft 122, for example. Attached to the stem 124 is a brace 126. The brace 126 may be hinged to the leg stem to allow the brace to pivot as needed. The brace 126 may be positioned against the patient's leg during use. FIGS. 3A and 3B show an embodiment of the positioning instrument 100 without the optional stabilizer component 120.

Figure 2A:
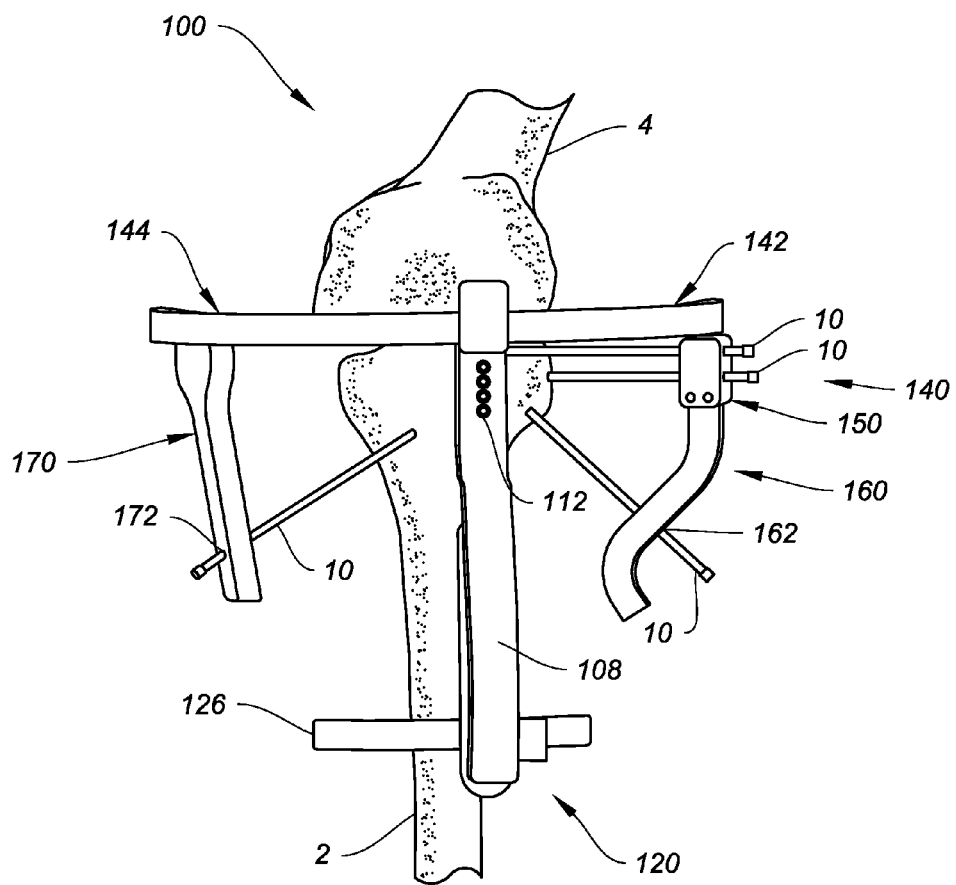
FIG. 2A is another perspective view of the positioning instrument of FIG. 1A in situ.
Figure 2B:
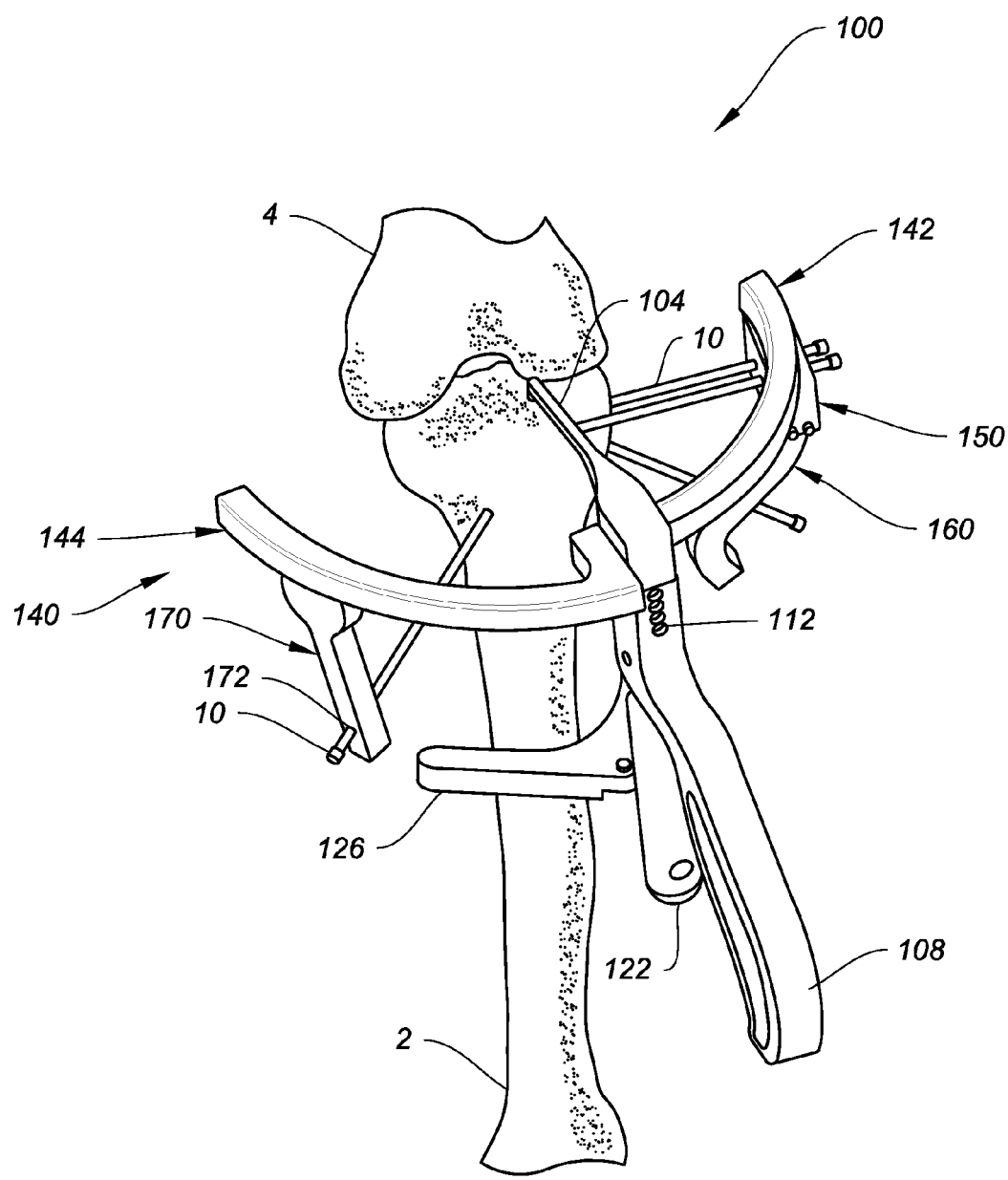
FIG. 2B is yet another perspective view of the positioning instrument of FIG. 1A in situ.

The positioning instrument 100 may also include a rail system 140 comprising a first rail arm 142 and a second rail arm 144, as shown in FIGS. 2A and 2B. Each of the rail arms 142, 144 may be configured to be detachable from the main body 102 of the positioning instrument 100. Accordingly, the positioning instrument 100 may be used with either one or both of the rail arms 142, 144. Further, each of the rail arms 142, 144 may be provided with an open slot 146 for receiving any one of a variety of alignment guides, such as a primary alignment guide 150 shown. Although not shown, primary alignment guide 150 may include a tab or other protrusion that would enable the guide 150 to attach to and slide along the first rail arm 142 within its open slot 146. This type of arrangement also allows the first rail arm 142 to be quickly and easily detached (i.e., slipped off) the guide 150 after the guide 150 has been independently secured to the bone 2.

While each of the rail arms 142, 144 is shown to be circular, it is contemplated that the rail arms 142, 144 may be provided with any other geometric configuration such as an L-shape, U-shape, C-shape, etc. so long as it is capable of supporting and positioning the primary alignment guide 150 adjacent to the bone to be treated.

Primary alignment guide 150 may serve as a jig, or a platform/frame to guide a device to a specific location on the bone 2 being treated. One or more device portals 152 may be provided on the primary alignment guide 150. Each portal 152 has a predetermined distance and spatial relationship relative to the other portals, such that the clinician can determine with accuracy the depth of the portal 152 relative to the indicator probe 104 and consequently the top surface of the bone 2. The portals 152 serve as spatial reference or orientation or location markers for the clinician. Moreover, the device portals 152 are configured to provide accurate and controlled delivery of a device to the target site.

The portals 152 may be configured at any desired angle relative to the alignment guide 150. In one embodiment, the portals 152 may be angularly configured to guide, or direct, the device in a parallel direction relative to the top of the bone being treated. In another embodiment, the portals 152 may be angularly configured to direct the device in a perpendicular direction relative to the top of the bone, for example. Thus, the positioning instrument 100 may be particularly suited to enable implants or other instruments to be inserted in a predetermined angular orientation to the top bone surface in an easy, fast and precise manner. In some instances, pins 10 may be placed through tool-receiving openings 154 provided on the primary alignment guide 150 to secure the guide 150 to the bone 2. However, it is understood that the tool-receiving opening 154 may also receive an insertion tool for the delivery of an implantable device or injectable material (such as a bone substitute material), and the device portal 152 may also receive a pin 10, if so desired. Accordingly, the surgeon may use the device portal 152 and the tool-receiving hole 154 interchangeably as needed.

A detachable inferior guide portion 160 may optionally be provided with the positioning instrument 100. The inferior guide portion 160 may include one or more tool-receiving holes 162 for receiving a tool. The tool may be, for example, a pin, needle or drill bit. In one instance, the tool may be a drill to drill a hole in the bone 2, for example. In another instance, the tool may be a device insertion tool for introduction of an implantable device, for example. Accordingly, the inferior guide portion 160 offers a distal, or inferior approach guide, for targeting the lower area of the target site or other tissue area from different angular approaches through tool-receiving holes 162. It is contemplated that any known mechanism for attaching the inferior guide portion 160 to the primary alignment guide 150 may be provided, so long as the mechanism allows quick and easy detachment, without disturbing any other components of the instrument 100 or tools that may have been employed during its use.

Turning now to FIGS. 2A and 2B, 3A and 3B, the second rail arm 144 may be seen. In this example, the joint is a knee joint and the upper bone is the femur 4, the lower bone being the tibia 2. The defect to be targeted is located in the tibia 2 near the contact surface. As shown in FIG. 3B, the second rail arm 144 may be offset with respect to the first rail arm 142 by a distance d. Accordingly, the second rail arm 144 may have a larger radius than first rail arm 142. Like first rail arm 142, the second rail arm 144 also includes an open slot 146 for receiving an alignment guide. This type of arrangement allows the second rail arm 144 to be quickly and easily removed from the alignment guide after the guide has been independently secured to the bone. In the exemplary embodiment shown, the second rail arm 144 may be configured to receive a transverse alignment guide 170.

Like primary alignment guide 150, the transverse alignment guide 170 may include a tab or other protrusion (not shown) to allow it to connect to and slide along the second rail arm 144. Further, similar to inferior guide portion 160, the transverse alignment guide 170 may include one or more tool-receiving holes 172 for receiving a tool. The tool may be, for example, a pin, needle or drill bit. In one instance, the tool may be a drill to drill a hole in the bone 2, for example. In another instance, the tool may be a device insertion tool for introduction of an implantable device, for example. Accordingly, the transverse alignment guide 170 offers a distal, or inferior approach guide, for targeting the lower area of the target site or other tissue area from a different angle, or location, with respect to the insertion site. In this case, the approach is from a transverse angle. For example, if the primary target area is the medial side of the knee, the transverse guide 170 would target the approach from the opposite or contralateral side of the same bone.

The positioning instrument 100 of the present disclosure provides several advantages, including simple, repeatable targeting of a defect in a bone for percutaneous treatment of that defect. The indicator probe 104 can be used arthroscopically to locate the defect visually from above the cartilage surface. The circular rail system 140 serves as a frame for a 3-dimensional reference system to locate the defect, while the various alignment guides and the corresponding device or tool-receiving holes allow for percutaneous targeting of the defect. In addition, reference from the probe 104 to the primary alignment guide 150 allows for repeatable targeting of the defect in the range of about 5-10 mm below the articular surface where the indicator probe 104 resides.

The positioning instrument 100 of the present disclosure is suitable for use where it is desirable to treat a local area specific to a defect being identified using a percutaneous approach near the defect. In one exemplary method of use, the positioning instrument 100 shown in FIGS. 1A and 2B with only the first rail arm 142 attached can be used to target a target area 6 local to a defect in a bone 2 for repair. First, the indicator probe 104 is used to locate the local area specific to the defect, or the target area 6, in the cartilage above the defect. The defect could be, for example, a bone marrow lesion in the subchondral region of the bone to be treated. The primary alignment guide 150 is then positioned along the circular rail system 140, specifically the first rail arm 142, to the desired location for a percutaneous approach to the target area 6. Pins 10 can be used to fix the primary alignment guide 150 to the bone 2 and the circular rail system 120 can be removed. Pins 10 can be inserted through the primary alignment guide 150 and into the target area 6. In addition, pins 10 can be inserted into the target area 6 from an inferior approach using the inferior guide portion 160. Once the pins 10 are fixed in the targeted positions, the primary alignment guide 150 and the inferior guide portion 160 can be removed, leaving only the pins 10 behind.

At this stage, a number of treatment modalities can be employed. Applicants have discovered that a number of treatment modalities, and associated devices, instruments and related methods of use for addressing these problems. In one treatment modality, the target area 6 local to the defect can be strengthened by introduction of a hardening material at the site. For example, polymethylmethacrylate (PMMA) or calcium phosphate (CaP) cement injections can be made at the defect site. PMMA injection may increase the mechanical strength of the bone, allowing it to withstand greater mechanical stresses. CaP cement injection may also increase the mechanical strength of the bone, while also stimulating the localized region for bone fracture repair. In one embodiment, the injection can be made parallel to the joint surface. In another embodiment, the injection can be made at an angle to the joint surface. In yet another embodiment, the injection can be made below the target area 6.

In another treatment modality, the target area 6 can be stimulated to improve the body's natural healing process. For example, in one embodiment of this treatment modality, small holes may be drilled at the region of the defect to increase stimulation (e.g., blood flow, cellular turnover, etc.) and initial bone repair. In another embodiment, after holes are drilled an osteogenic, osteoinductive, or osteoconductive agent may be introduced to the site. Bone graft material, for example, may be used to fill the hole. This treatment modality may create a better load supporting environment leading to long term healing.

In yet another treatment modality, an implantable device may be implanted into target area 6 to provide mechanical support to the damaged or affected bone region, such as where an insufficiency fracture has occurred. The implant may help create a better load distribution in the subchondral region. In the knees, the implant may support tibio-femoral compressive loads. In addition, the implant may mechanically integrate sclerotic bone with the surrounding healthy bone tissue.

While each of the above-mentioned treatment modalities may be administered independent of one another, it is contemplated that any combination of these modalities may be applied together and in any order so desired, depending on the severity or stage of development of the bone defect(s).

In another exemplary method of use, the positioning instrument 100 of FIGS. 2A, 2B, 3A and 3B with both the first and second rail arms 142, 144 attached can be used to target a target area 6 from multiple angles, or locations. In one exemplary method of treating a defect of a bone, the surgeon may identify the defect using MRI or other imaging technology. Once identified, either arthroscopically or through imaging technology, the surgeon can secure the positioning instrument 100 in place by securing pins 10 through the tool-receiving holes of the main body 102 and/or the alignment guide 150. The brace 126 may be positioned against a portion of the patient's lower leg, in the case of a knee joint. After the positioning instrument 100 is stably secured, the surgeon may elect to insert a drill bit through one of the device portals 152 and drill a hole or cavity proximate to the defect. The surgeon may decide that drilling a cavity is sufficient treatment and after the cavity is created, the drill bit can be removed and the procedure complete.

Figure 4:
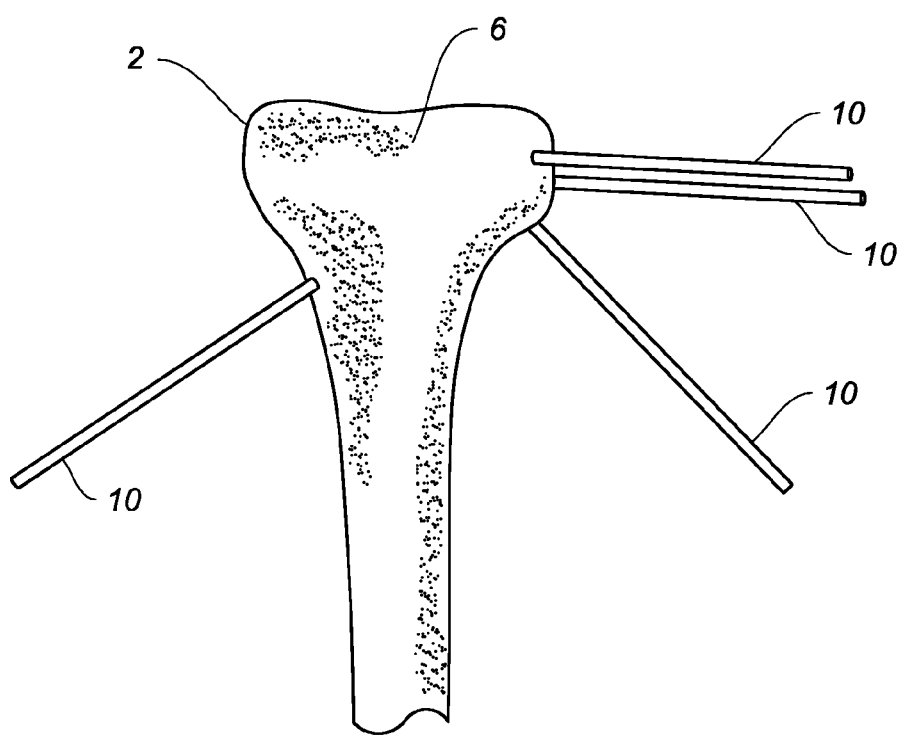
FIG. 4 represents pin placement in a partial bone using the positioning instrument of the present invention.

If the surgeon elects to perform additional steps to treat the defect, the surgeon may elect to repeat these steps using the tool-receiving holes of either or both the inferior guide portion 160 and transverse alignment guide 170 to access and target the defect from various angles and locations. For instance, in addition to the steps mentioned above, or in substitution to the step of inserting a pin 10 from an inferior approach through the inferior guide portion 160, the transverse alignment guide 170 may be positioned along the second rail arm 144 to the desired location for a transverse approach to the target area 6. Pins 10 can be used to fix the transverse alignment guide 170 to the bone 2 before removing the second rail arm 144. The proper positioning of the pins 10 can be similar to that shown in FIG. 4. Any of the pins 10 may be substituted for K-wires so that additional instruments and tools may be applied through the tool-receiving holes 162, 172. Subsequently, the treatment modalities mentioned earlier can be employed. Alternatively, it is contemplated that the inferior guide portion 160 and the transverse alignment guide 170 may be utilized to assist with the drilling of cavities into the bone through their respective tool-engaging holes 162, 172. If the surgeon elects to perform additional treatment steps, he could insert an injectable material and/or an implantable device into the pre-drilled cavities.

As can be seen in FIG. 3B, a contralateral, or transverse approach to the target area 6 allows for a more direct, normal angular approach of any kind of implantable device into the bone 2 instead of a shallow angular approach that can happen when directing an implantable device from an inferior or distal approach into the target area 6 on the same side. Another benefit of a transverse approach to the target area 6 is the avoidance of weakening the bone on the same side of the defect for defects that reside near the periphery of the bone. For example, by avoiding approaching the defect from an inferior angle to the same side near the periphery, the user avoids possible breakage of the bone from a shallow angle approach.

In addition, since the transverse approach allows the user to span across a greater area of bone, there is more opportunity to adjust the depth of any drill or insertion near the target area 6. This offers less risk compared to a smaller bone depth on the same side of the bone with an inferior approach. The ability to approach the defect or target site through a greater area of bone also provides the opportunity to compact more bone tissue at the target site. In other words, by approaching the target site from a contralateral side of the bone, more bone tissue can be compacted towards the target site. The process of compacting bone tissue at the target site may be a treatment modality by itself. Since the positioning instrument 100 of the present disclosure provides the advantage of precise and repeated access to a target site from a variety of angles, the positioning instrument 100 may be used to compact bone tissue at the target site from multiple approaches, or angles, creating a starburst-like pattern.

Figure 5A:
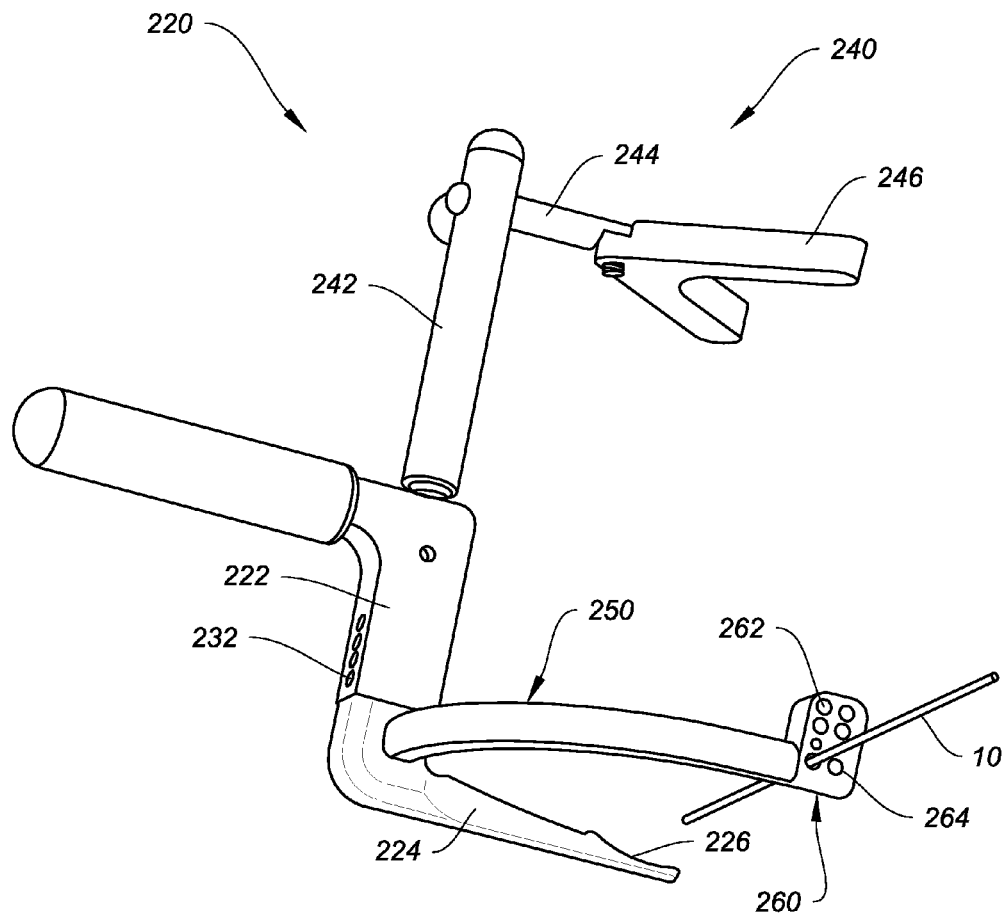
FIG. 5A is a perspective view of an exemplary embodiment of a positioning instrument of the present disclosure.
Figure 5B:
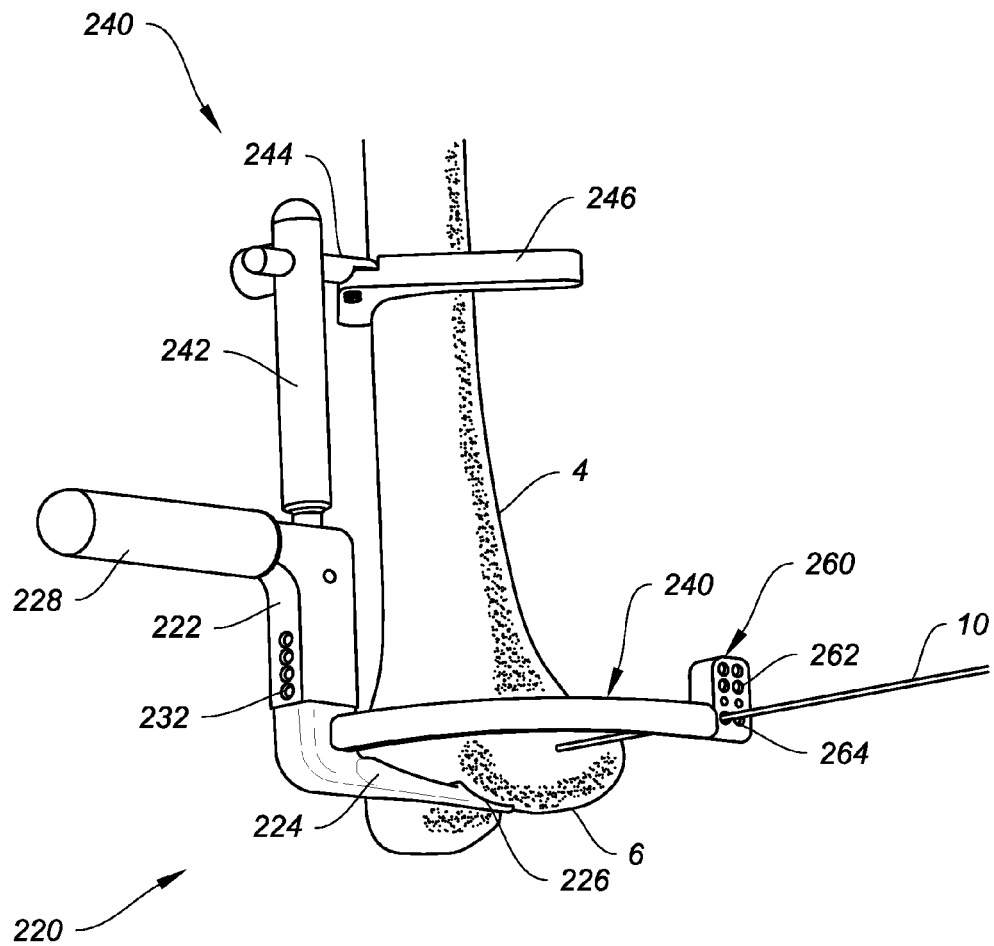
FIG. 5B shows the positioning instrument of FIG. 5A in situ.

FIGS. 5A and 5B show another exemplary embodiment of a positioning instrument 220 of the present disclosure. The positioning instrument 220 enables repeatable, controlled delivery of a device to a target area in the bone. As shown, the device may be a pin 10. However, the term "device" is used herein to refer generally to any number of implantable devices, materials and instruments suitable for bone treatment and/or repair. As will be described in more detail below, the device may be an implantable device, an insertion tool, a drill bit, an injection needle, a catheter, or any other surgical instrument. Accordingly, the positioning instrument 220 may be used to provide quick, easy, accurate and repeatable targeting of a specific bone defect for a number of instruments or implants that can perform any variety of treatment functions.

The positioning instrument 220 may comprise a main body 222 from which a support arm 224 extends in a generally perpendicular angle from one end of the main body 222. The support arm 224 terminates into an indicator probe, contoured seat, or rest, 226 that is suited for placement against a condyle of a femur 4, as shown in FIG. 5B. In one example, the support arm 224 could serve as an indicator probe to be used as a visual pointer to indicate a possible visible area of a defect on the condyle of the femur 4. At an opposite end of the main body 222 a handle 228 may also extend generally perpendicular to the body 222. Tool-receiving holes 232 may be provided on the main body 222 for receiving a tool such as a pin, wire, or needle, for example. The tool may be one that is suitable to secure the main body 222 to the femur 4. However, the tool may also easily be an insertion tool for the delivery of an implantable device or injectable material to the femur 4, if so desired.

An optional stabilizer component 240 may be provided with the positioning instrument 220. The stabilizer component 240 may be detachable, and include a shaft 242 that can be quickly and easily attached or removed from the main body 222. It is contemplated that the shaft 242 may be configured to be adjustable in length relative to the main body 222 to accommodate different sized patients. The shaft 242 can receive a stem 244 that is configured to be angularly adjustable relative to the shaft 242. Attached to the stem 244 is a brace 246 configured for placement against a bone surface, such as the patient's leg, as shown in FIG. 5B. The brace 246 may be hinged to the stem 244 to allow the brace 246 to pivot as needed.

The positioning instrument 220 may also include a rail 250 extending from the main body 222 of the instrument 220. The rail 250 may be circular, as shown, or any other geometric configuration such as an L-shape, U-shape, C-shape, etc. The rail 250 may be configured to receive an alignment guide 260. The alignment guide 260 may serve as a jig, or a platform/frame to guide any kind of instrument, tool or device to a specific location on the bone 4 being treated. The alignment guide 260 may be configured to be detachable from the rail 250 during use.

One or more device portals 262 may be provided on the alignment guide 260. Each portal 262 has a predetermined distance and spatial relationship relative to the other portals, such that the clinician can determine with accuracy the depth of the portal 262 relative to the rail 250 and consequently the bone surface of the bone 4 being treated. The portals 262 serve as spatial references or orientation or location markers for the clinician. Moreover, the device portals 262 are configured to allow repeated, accurate and controlled delivery of a device to the target site.

The alignment guide 260 may additionally include tool-receiving holes 264 for receiving a tool such as a pin, wire, or needle, for example. The tool may be one that is suitable to secure the guide 260 to the femur 4. However, the tool may also easily be an insertion tool for the delivery of an implantable device or injectable material to the femur 4, if so desired. Accordingly, the surgeon may use the device portal 262 and the tool-receiving hole 264 interchangeably as needed.

In use, the positioning instrument 220 can be placed such that the contoured seat 226 rests against a bone surface of the femur 4, as shown in FIG. 5B. The optional stabilizer component 240 may be used to stabilize the positioning instrument 220 against the patient's leg during surgery. One or more pins 10, such as the one shown, may be used to secure one or more portions of the positioning instrument 220 to the femur 4, such as by placement through the tool-receiving holes 232, 264 of the main body 222 or alignment guide 260. After the positioning instrument 220 has been secured, the surgeon may elect to insert a device through one of the device portals 262 of the alignment guide to a target site on the femur 4. The surgeon may repeat the procedure again, or multiple times, using the same device portal 262. Alternatively, or in addition, the surgeon may perform another procedure by placing a device through another device portal 262 on the alignment guide 260. Accordingly, the positioning instrument 220 of the present disclosure allows repeated, accurate, precise and easy targeting of an area to be treated on the femur 4. The positioning instrument 220 is especially helpful in providing the surgeon with the ability to repeatedly and accurately target an area of the femur 4 near the bone surface from the side, where space is limited and the ability to navigate the patient's natural anatomy at this region provides challenges to the treatment of a defect close to the bone surface.

Figure 6A:
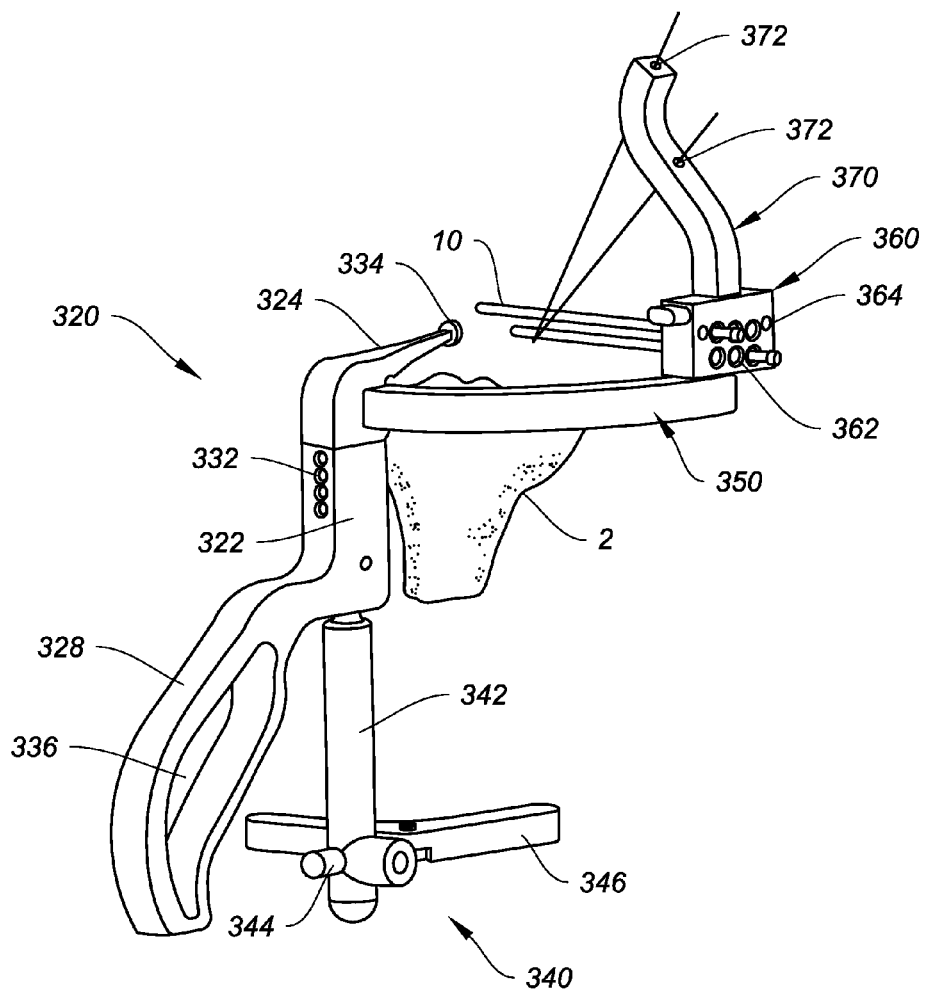
FIG. 6A is a perspective front view of another exemplary embodiment of a positioning instrument of the present disclosure in use with a partial bone.
Figure 6B:
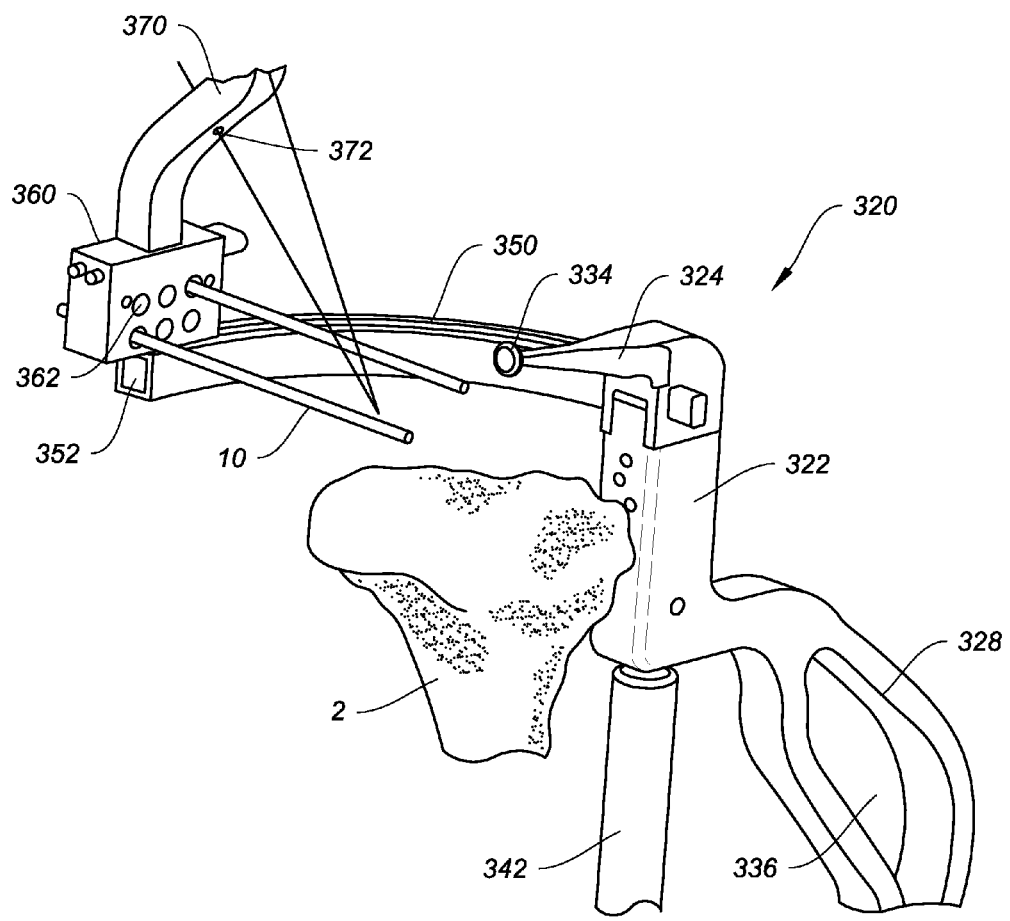
FIG. 6B is a perspective rear view of the positioning instrument of FIG. 2A in use with a partial bone.
Figure 7A:
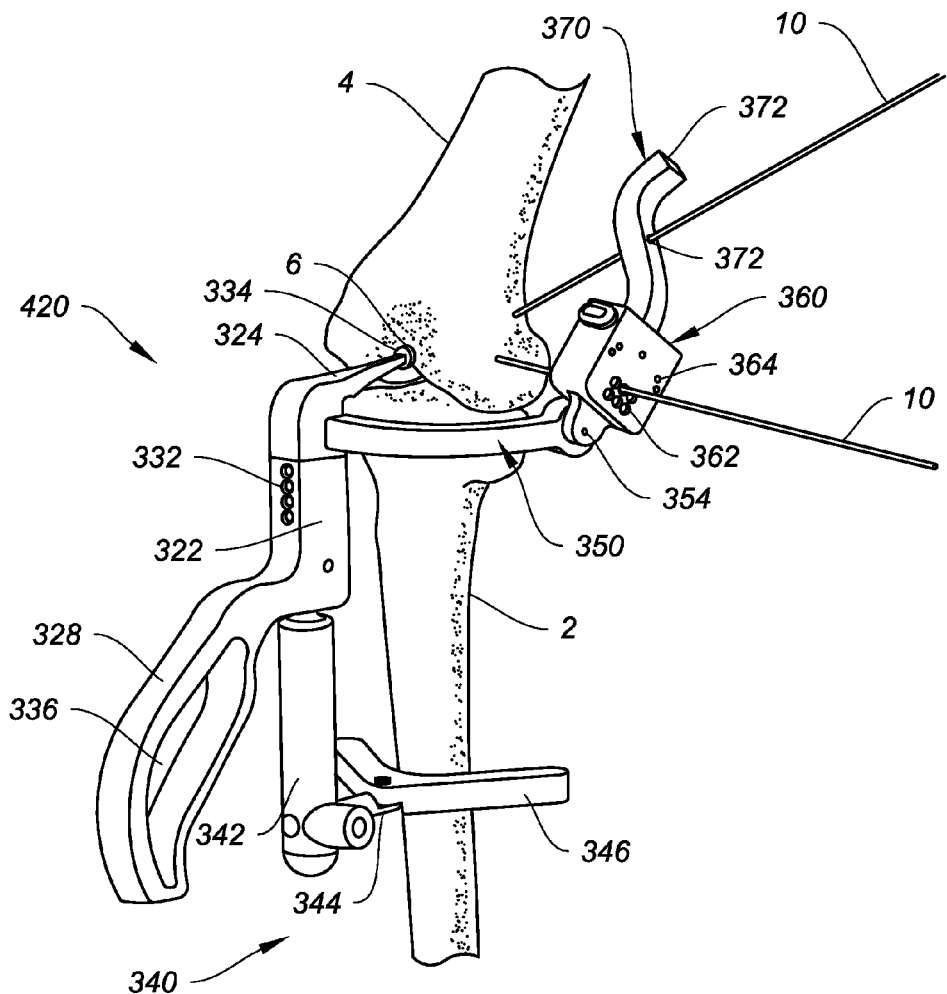
FIG. 7A is a perspective view of yet another exemplary embodiment of a positioning instrument of the present disclosure in situ.
Figure 7B:
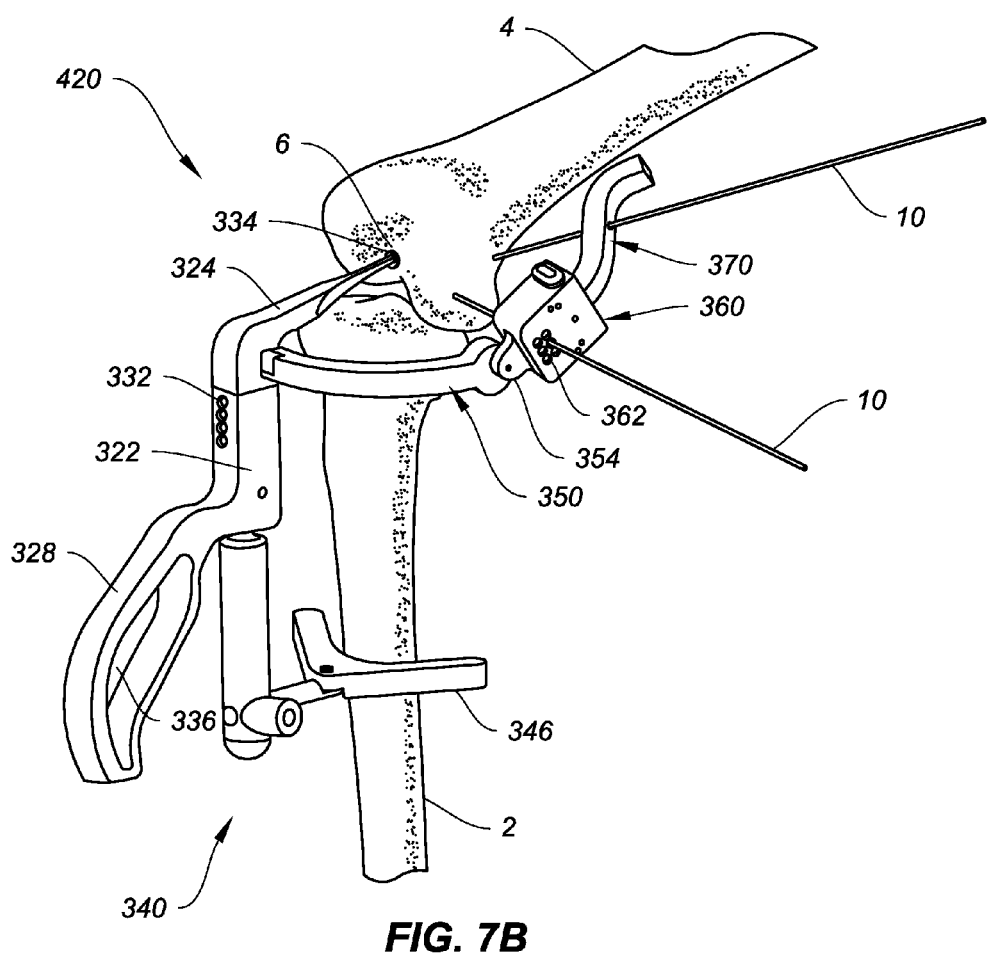
FIG. 7B is another perspective view of the positioning instrument of FIG. 6A in use with a flexed joint.

FIGS. 6A and 6B illustrate another exemplary embodiment of a positioning instrument 320 of the present disclosure. The positioning instrument 320 is similar to positioning instrument 220. As with positioning instrument 220, positioning instrument 320 may comprise a main body 322, a support arm 324 that extends in a generally perpendicular angle from one end of the main body 322, and a handle 328 also extending generally perpendicular to the body 322 from an opposite end. In this embodiment, the support arm 324 may terminate in a bumper 334 that can be configured to provide a cushion against a bone surface. The bumper 334 may also be configured as, for example, a rounded knob, suction cup or plunger for placement against a bone. Additionally, the bumper 334 may serve as an indicator probe to be used as a visual pointer to indicate a possible visible area of a defect on the condyle of the femur 4 (not shown). Although the femur 4 is not shown in FIGS. 6A and 6B, it is understood that the bumper 334 may rest against the condyle of the femur 4 as shown in FIGS. 7A and 7B.

The main body 322 of positioning instrument 320 may also be provide with tool-receiving holes 332 for receiving a tool such as a pin, wire, or needle, for example, to secure the positioning instrument 320 to the bone. In this particular embodiment, the positioning instrument 320 may be secured to the lower leg. In addition, the handle 328 may include a cutout portion 336 for ease of gripping the instrument 320.

An optional stabilizer component 340 may be provided with the positioning instrument 320. The stabilizer component 340 may be detachable, and include a shaft 342 that can be quickly and easily attached or removed from the main body 322 of the positioning instrument 320. The shaft 342 may be configured to be adjustable in length relative to the main body 322 to accommodate different sized patients. The shaft 342 can receive a stem 344 that is configured to be angularly adjustable relative to the shaft 342. Attached to the stem 344 is a brace 346 configured for placement against a body surface, such as the patient's leg. Though not shown in FIGS. 6A and 6B, the brace 346 may be configured to rest against the patient's lower leg. The brace 346 may be hinged to the stem 344 to allow the brace 346 to adjustably pivot as needed.

The positioning instrument 320 may also include a rail 350 extending from the main body 322 of the instrument 320. The rail 350 may be circular, as shown, or any other geometric configuration such as an L-shape, U-shape, C-shape, etc. The rail 350 may be configured to receive an alignment guide 360 on its upper surface, as shown in FIGS. 6A and 6B. In one embodiment, the rail 350 may be provided with an open slot 352 for receiving a protrusion or other extension (not shown) on the alignment guide 360. The alignment guide 360 may be slidable and detachable from this open slot 352 of the rail 350.

The alignment guide 360 may contain one or more device portals 362, with each portal 362 having a predetermined distance and spatial relationship relative to the other portals, such that the clinician can determine with accuracy the depth of the portal 362 relative to the rail 350 and consequently the bone surface of the bone to be treated. The alignment guide 360 may additionally include tool-receiving holes 364 for receiving a tool such as a pin, wire, or needle, for example. The tool may be one that is suitable to secure the guide 360 to the upper bone of the joint. However, the tool may also easily be an insertion tool for the delivery of an implantable device or injectable material to the upper bone, if so desired. Accordingly, the surgeon may use the device portal 362 and the tool-receiving hole 364 interchangeably as needed.

A detachable superior guide component 370 may optionally be provided with the positioning instrument 320, as shown in FIGS. 6A and 6B. The superior guide component 370 may include one or more tool-receiving holes 372 for receiving a tool. The tool may be, for example, a pin, needle or drill bit. In one instance, the tool may be a drill to drill a hole in the femur 4 (not shown), for example. In another instance, the tool may be a device insertion tool for introduction of an implantable device, for example. Accordingly, the superior guide component 370 offers a proximal, or superior approach guide, for targeting the upper area of the target site or other tissue area from different angular approaches through tool-receiving holes 372. It is contemplated that any known mechanism for attaching the superior guide component 370 to the alignment guide 350 may be provided, so long as the mechanism allows quick and easy detachment, without disturbing any other components of the instrument 320 or tools that may have been employed during its use.

Unlike positioning instrument 220, this positioning instrument 320 allows the surgeon to locate, access and target a defect area on the upper bone of a joint while bracing against the lower portion of the joint. As seen in FIGS. 6A and 6B, the alignment guide 360 resides above the rail 350, allowing the surgeon to position the alignment guide 360 along the rail 350 and relative to the top bone of a joint, for predetermined angular orientation of the instruments, tools or devices to the target area on the upper bone. In the case of a knee joint, the ability to brace against the lower limb while targeting the femur provides the surgeon with the advantage of having less pins and extended hardware in the upper area, which would limit visual access as well as surgical access to the femur. By bracing below the femur, the surgeon can free up more working space around the femur. An additional advantage is that the surgeon can pivot the lower limb to a certain angle to position the instrument 320 at a certain location on the upper limb, using the stability of the brace 346 against the lower limb while treating the upper limb.

FIGS. 7A and 7B illustrate yet another exemplary embodiment of a positioning instrument 420 of the present disclosure. Positioning instrument 420 may comprise a main body 322, a support arm 324 that extends in a generally perpendicular angle from one end of the main body 322, and a handle 328 also extending generally perpendicular to the body 322 from an opposite end. Like positioning instrument 320, the support arm 324 may terminate in a bumper 334 that can be configured to provide a cushion against a bone surface, such as the contact surface 6 of the femur 4, as shown in FIGS. 6A and 6B. The bumper 334 may also be configured as, for example, a rounded knob, suction cup or plunger for placement against a bone.

The main body 322 of positioning instrument 420 may also be provide with tool-receiving holes 332 for receiving a tool such as a pin, wire, or needle, for example, to secure the positioning instrument 420 to the lower portion of the joint. For example, in the knee joint shown, the positioning instrument 420 may be secured to the patient's lower leg using pins through the tool-receiving holes 332, if desired. In addition, the handle 328 may include a cutout portion 336 for ease of gripping the instrument 420.

Again, an optional stabilizer component 340 may be provided with the positioning instrument 420. The stabilizer component 340 may be detachable, and include a shaft 342 that can be quickly and easily attached or removed from the main body 322 of the positioning instrument 420. The shaft 342 may be configured to be adjustable in length relative to the main body 322 to accommodate different sized patients. The shaft 342 can receive a stem 344 that is configured to be angularly adjustable relative to the shaft 342. Attached to the stem 344 is a brace 346 configured for placement against a body surface, such as the patient's leg. As shown, the brace 346 may be configured to rest against the patient's lower leg. The brace 346 may be hinged to the stem 344 to allow the brace 346 to adjustably pivot as needed.

The positioning instrument 420 may also include a rail 350 extending from the main body 322 of the instrument 420. The rail 350 may be circular, as shown, or any other geometric configuration such as an L-shape, U-shape, C-shape, etc. The rail 350 may be configured to receive an alignment guide 360 on its upper surface. In order to provide another range of motion, the alignment guide 360 of instrument 420 may be attached to the rail 350 at a hinged connection 354 that would enable the alignment guide 360 to pivot relative to the rail 350, as shown in FIGS. 7A and 7B.

The alignment guide 360 may contain one or more device portals 362, with each portal 362 having a predetermined distance and spatial relationship relative to the other portals, such that the clinician can determine with accuracy the depth of the portal 362 relative to the rail 350 and consequently the bone surface of the bone to be treated. The alignment guide 360 may additionally include tool-receiving holes 364 for receiving a tool such as a pin, wire, or needle, for example. The tool may be one that is suitable to secure the guide 360 to the upper bone of the joint. However, the tool may also easily be an insertion tool for the delivery of an implantable device or injectable material to the upper bone, if so desired. Accordingly, the surgeon may use the device portal 362 and the tool-receiving hole 364 interchangeably as needed.

As shown, a detachable superior guide component 370 may optionally be provided with the positioning instrument 420. The superior guide component 370 may include one or more tool-receiving holes 372 for receiving a tool. The tool may be, for example, a pin, needle or drill bit. In one instance, the tool may be a drill to drill a hole in the femur 4, for example. In another instance, the tool may be a device insertion tool for introduction of an implantable device, for example. Accordingly, the superior guide component 370 offers a proximal, or superior approach guide, for targeting the upper area of the target site or other tissue area from different angular approaches through tool-receiving holes 372. It is contemplated that any known mechanism for attaching the superior guide component 370 to the alignment guide 360 may be provided, so long as the mechanism allows quick and easy detachment, without disturbing any other components of the instrument 420 or tools that may have been employed during its use.

Similar to positioning instrument 320, this positioning instrument 420 allows the surgeon to locate, access and target a defect area on the upper bone of a joint while bracing against the lower portion of the joint. The ability to brace against the lower leg while targeting the femur 4 provides the surgeon with the advantage of having less pins and extended hardware in the upper area, which would limit visual access as well as surgical access to the femur. By bracing below the femur, the surgeon can free up more working space around the femur. Additionally, since the alignment guide 360 of instrument 420 is able to pivot, it is possible to flex the joint (see FIG. 7B) and still maintain the ability to repeatedly, accurately, easily and precisely locate a target site on the upper bone (femur 4) of the joint. In other words, the alignment guide 360 is able to move along with the upper bone of the joint.

In the illustrated examples described above, the upper bone may be a femur for a knee joint repair. It is understood, however, that the positioning instruments of the present disclosure may be applied to an upper bone found in any body joint, such as a hip, ankle or shoulder, etc.

In one exemplary method of treating a defect on an upper bone of a joint in the subchondral area near the contact surface, the surgeon may identify the defect using MRI or other imaging technology. Once identified, either arthroscopically or through imaging technology, the surgeon can secure the positioning instrument 220, 320, 420 in place by securing pins 10 through the tool-receiving holes of the main body and/or the alignment guide. The brace may be positioned against a portion of the upper part or lower part of a patient's lower limb, or leg, in the case of a knee joint. After the positioning instrument 220, 320, 420 is stably secured, the surgeon may elect to insert a drill bit through one of the device portals and drill a hole or cavity proximate to the defect. The surgeon may decide that drilling a cavity is sufficient treatment and after the cavity is created, the drill bit can be removed and the procedure complete. Alternatively, or in addition, the surgeon may elect to compact bone tissue at the target site as a treatment modality. Using the positioning instrument of the embodiments to repeatedly, easily and accurately target the area near the defect, the surgeon can approach the target site from a number of different locations (i.e., device portals) or angles (i.e., by adjusting the alignment guide), creating a geometric pattern around the defect, such as a starburst, for example.

If the surgeon elects to perform additional steps to treat the defect, then the surgeon may elect to insert an implantable device through the same device portal into the cavity. This would be accomplished by introducing an insertion tool with the implantable device attached through the alignment guide in a similar manner above. Alternatively, or in addition, the surgeon may insert an injectable material through the device portal and into the cavity or inside, above, below, beside, or around the implantable device. The surgeon may elect to repeat these steps using the tool-receiving holes and the superior guide component 370 to access and target the defect from various angles and locations. The entire method could be employed in a percutaneous fashion if so desired.

Other embodiments will be apparent to those skilled in the art from consideration of the specification and practice of the embodiment disclosed herein. It is intended that the specification and examples be considered as exemplary only, with a true scope and spirit of the embodiment being indicated by the following claims.

What is claimed is:

1. A positioning instrument for controlled delivery of a device to a target site of a bone, comprising:
a main body extending at one end into an indicator probe and at an opposite end into a handle, the indictor probe having a terminal end configured for external placement on a bone surface to assist with visual identification of the target site of the bone while preserving the bone surface;
a rail extending from the main body; and
an alignment guide having a device portal for insertion of a device therethrough, the alignment guide being detachable and movable along a length of the rail, the device portal defining a trajectory,
wherein the device portal is configured to provide delivery of the device to the target site indicated by the indicator probe, and
wherein the trajectory of the device portal does not intersect with the terminal end of the indicator probe.

2. The instrument of claim 1, wherein the alignment guide includes a plurality of device portals.

3. The instrument of claim 2, wherein each device portal has a predetermined spatial relationship relative to each other.

4. The instrument of claim 1, wherein the alignment guide further includes a hole for insertion of a tool.

5. The instrument of claim 4, wherein the tool is a pin, needle, or drill.

6. The instrument of claim 1, further including an inferior guide portion extending from the alignment guide.

7. The instrument of claim 6, wherein the inferior guide portion is detachable from the alignment guide.

8. The instrument of claim 7, wherein the inferior guide portion includes a hole for insertion of a tool.

9. The instrument of claim 1, further including a superior guide component extending from the alignment guide.

10. The instrument of claim 9, wherein the superior guide component includes a hole for insertion of a tool.

11. The instrument of claim 1, further including a pair of rails, each rail extending in opposite directions from the main body and having a free end.

12. The instrument of claim 11, further including a pair of alignment guides, each guide being detachable and movable along a length of one of the rails.

13. The instrument of claim 12, wherein one of the alignment guides is configured for a contralateral approach to the target site.

14. The instrument of claim 11, wherein one of the rails has a larger radius than the other rail.

15. The instrument of claim 1, wherein the device is an implantable device.

16. The instrument of claim 1, wherein the device is an insertion tool, drill, injection needle, or catheter.

17. The instrument of claim 1, wherein the rail is circular.

18. The instrument of clam 1, wherein the rail extends around the target site.

19. A method for treating a bone defect, comprising:
providing a positioning instrument for controlled delivery of a device to a target site in the bone tissue, the positioning instrument comprising a main body extending at one end into an indicator probe, and at an opposite end into a handle, the indicator probe having a terminal end configured for external placement on a bone surface to assist with visual identification of the target site of the bone while preserving the bone surface; a rail extending from the main body; and an alignment guide having a device portal for insertion of a device therethrough, the alignment guide being detachable and movable along a length of the rail, wherein the device portal defines a trajectory that does not intersect with the terminal end of the indicator probe; and
introducing a device through the device portal of the alignment guide and to the target site.

20. The method of claim 19, further including the step of placing the indicator probe adjacent the target site.

21. The method of claim 19, further including the step of positioning one alignment guide along a side of the bone near the target site, and positioning another alignment guide on a contralateral side of the bone.

22. The method of claim 21, further including the step of introducing a device through at least one of the device portals of each of the alignment guides.

23. The method of claim 22, wherein at least one device is introduced in a transverse inferior approach to the target site.

24. The method of claim 19, wherein the device is a cavity creation tool and further including the step of creating a cavity at the target site.

25. The method of claim 19, further including the step of attaching an implantable device to an insertion tool and introducing the insertion tool through the device portal to the target site.

26. The method of claim 19, further including the steps of introducing an injection catheter through the device portal and injecting a material to the target site.

27. The method of claim 19, wherein the material is a bone void filler, bone cement, biological agent, or a curable material.

28. The method of claim 19, wherein the target site is near a bone defect, the defect including a bone marrow lesion, edema, sclerotic bone, fracture, or fissure.

29. The method of claim 19, wherein the bone defect is located in subchondral bone.

30. The method of claim 29, wherein the subchondral bone is at a knee, hip, ankle, or shoulder joint.

31. The method of claim 29, wherein the bone defect is located near an articular surface.

32. A positioning instrument for controlled delivery of a device to a target site, comprising:
a main body extending at one end into an indicator probe for visual determination of a target site of a bone, and at an opposite end into a handle;
a rail extending from the main body;
an alignment guide having a device portal for insertion of a device therethrough, the alignment guide being detachable and movable along a length of the rail; and
further including an inferior guide portion extending from the alignment guide, the inferior guide portion being detachable from the alignment guide;
wherein the device portal is configured to provide delivery of the device to the target site indicated by the indicator probe.

33. A positioning instrument for controlled delivery of a device to a target site, comprising:
a main body extending at one end into an indicator probe for visual determination of a target site of a bone, and at an opposite end into a handle;
a rail extending from the main body;
an alignment guide having a device portal for insertion of a device therethrough, the alignment guide being detachable and movable along a length of the rail; and
further including an inferior guide portion extending from the alignment guide, the inferior guide portion being detachable from the alignment guide and including a hole for insertion of a tool;
wherein the device portal is configured to provide delivery of the device to the target site indicated by the indicator probe.

34. A positioning instrument for controlled delivery of a device to a target site, comprising:
a main body extending at one end into an indicator probe for visual determination of a target site of a bone, and at an opposite end into a handle;
a rail extending from the main body;
an alignment guide having a device portal for insertion of a device therethrough, the alignment guide being detachable and movable along a length of the rail; and
further including a superior guide component extending from the alignment guide, the superior guide component including a hole for insertion of a tool;
wherein the device portal is configured to provide delivery of the device to the target site indicated by the indicator probe.

35. A positioning instrument for controlled delivery of a device to a target site, comprising:
a main body extending at one end into an indicator probe for visual determination of a target site of a bone, and at an opposite end into a handle;
a pair of rails, each rail extending in opposite directions from the main body and having a free end; and
an alignment guide having a device portal for insertion of a device therethrough, the alignment guide being detachable and movable along a length of the rail;
wherein the device portal is configured to provide delivery of the device to the target site indicated by the indicator probe.

36. A positioning instrument for controlled delivery of a device to a target site, comprising:
a main body extending at one end onto an indicator probe for visual determination of a target site of a bone, and at an opposite end into a handle;
a pair of rails, each rail extending in opposite directions from the main body and having a free end;
an alignment guide having a device portal for insertion of a device therethrough, the alignment guide being detachable and movable along a length of the rail; and
further including a pair of alignment guides, each guide being detachable and movable along a length of one of the rails;
wherein the device portal is configured to provide delivery of the device to the target site indicated by the indicator probe.

37. A positioning instrument for controlled delivery of a device to a target site, comprising:
a main body extending at one end into an indicator probe for visual determination of a target site of a bone, and at an opposite end into a handle;
a pair of rails, each rail extending in opposite direction from the main body and having a free end;

an alignment guide having a device portal for insertion of a device therethrough, the alignment guide being detachable and movable along a length of the rail; and further including a pair of alignment guides, each guide being detachable and movable along a length of one of the rails;

wherein one of the alignment guides is configured for a contralateral approach to the target site; and further wherein the device portal is configured to provide delivery of the device to the target site indicated by the indicator probe.

38. A positioning instrument for controlled delivery of a device to a target site, comprising:

a main body extending at one end into an indicator probe for visual determination of a target site of a bone, and at an opposite end into a handle;

a pair of rails, each rail extending in opposite directions from the main body and having a free end, wherein one of the rails has a larger radius than the other rail; and an alignment guide having a device portal for insertion of a device therethrough, the alignment guide being detachable and movable along a length of the rail;

wherein the device portal is configured to provide delivery of the device to the target site indicated by the indicator probe.

39. A method for treating a bone defect, comprising:

providing a positioning instrument for controlled delivery of a device to a target site in the bone tissue, the positioning instrument comprising a main body extending at one end into an indicator probe for visual determination of a target site of a bone to be treated, and at an opposite end into a handle; a rail extending from the main body; and an alignment guide having a device portal for insertion of a device therethrough, the alignment guide being detachable and movable along a length of the rail;

positioning one alignment guide along a side of the bone near the target site, and positioning another alignment guide on a contralateral side of the bone; and introducing a device through the device portal of one of the alignment guides and to the target site.

40. A method for treating a bone defect, comprising:

providing a positioning instrument for controlled delivery of a device to a target site in the bone tissue, the positioning instrument comprising a main body extending at one end into an indicator probe for visual determination of a target site of a bone to be treated, and at an opposite end into a handle; a rail extending from the main body; and an alignment guide having a device portal for insertion of a device therethrough, the alignment guide being detachable and movable along a length of the rail;

positioning one alignment guide along a side of the bone near the target site, and positioning another alignment guide on a contralateral side of the bone; and further including the step of introducing a device through at least one of the device portals of each of the alignment guides and to the target site.

41. A method for treating a bone defect, comprising:

providing a positioning instrument for controlled delivery of a device to a target site in the bone tissue, the positioning instrument comprising a main body extending at one end into an indicator probe for visual determination of a target site of a bone to be treated, and at an opposite end into a handle; a rail extending from the main body; and an alignment guide having a device portal for insertion of a device therethrough, the alignment guide being detachable and movable along a length of the rail;

positioning one alignment guide along a side of the bone near the target site, and positioning another alignment guide on a contralateral side of the bone; and introducing a device through the device portal of one of the alignment guides and to the target site;

wherein at least one device is introduced in a transverse inferior approach to the target site.

42. A method for treating a bone defect, comprising:

providing a positioning instrument for controlled delivery of a device to a target site in the bone tissue, the positioning instrument comprising a main body extending at one end into an indicator probe for visual determination of a target site of a bone to be treated, and at an opposite end into a handle; a rail extending from the main body; and an alignment guide having a device portal for insertion of a device therethrough, the alignment guide being detachable and movable along a length of the rail; and attaching an implantable device to an insertion tool and introducing the insertion tool through the device portal to the target site.

* * * * *

UNITED STATES PATENT AND TRADEMARK OFFICE
CERTIFICATE OF CORRECTION

PATENT NO. : 8,906,032 B2  
APPLICATION NO. : 12/950154  
DATED : December 9, 2014  
INVENTOR(S) : Hanson et al.

Page 1 of 1

It is certified that error appears in the above-identified patent and that said Letters Patent is hereby corrected as shown below:

On the Title Page

On page 3, in column 2, under "Other Publications", line 35, delete "Feb." and insert --Dec.--, therefor In the Claims In column 18, line 17, in Claim 1, delete "indictor" and insert --indicator--, therefor Signed and Sealed this  
Seventh Day of April, 2015

Michelle K. Lee  
*Director of the United States Patent and Trademark Office*